US011730482B2

United States Patent
Guerrera et al.

(10) Patent No.: US 11,730,482 B2
(45) Date of Patent: Aug. 22, 2023

(54) INSERTS, SPLINES, AND METHODS FOR REDUCING AND/OR ELIMINATING SPLINE CRASH IN SURGICAL INSTRUMENTS

(71) Applicant: Covidien LP, Mansfield, MA (US)

(72) Inventors: Joseph M. Guerrera, Watertown, CT (US); Charles R. Kollar, Washington, DC (US); Anthony Sgroi, Jr., Wallingford, CT (US); Justin Williams, Southbury, CT (US); Steven H. Joyce, Durham, CT (US); Christopher P. Penna, Guilford, CT (US); Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 288 days.

(21) Appl. No.: 17/293,117

(22) PCT Filed: Dec. 2, 2019

(86) PCT No.: PCT/US2019/063930
§ 371 (c)(1),
(2) Date: May 12, 2021

(87) PCT Pub. No.: WO2020/123169
PCT Pub. Date: Jun. 18, 2020

(65) Prior Publication Data
US 2022/0008076 A1    Jan. 13, 2022

Related U.S. Application Data

(60) Provisional application No. 62/779,727, filed on Dec. 14, 2018, provisional application No. 62/779,759, (Continued)

(51) Int. Cl.
*A61B 17/064* (2006.01)
*A61B 17/115* (2006.01)
*A61B 17/072* (2006.01)

(52) U.S. Cl.
CPC . *A61B 17/1155* (2013.01); *A61B 2017/07257* (2013.01); *A61B 2017/07271* (2013.01)

(58) Field of Classification Search
CPC ....... A61B 1/31; A61B 17/068; A61B 17/115; A61B 17/1114; A61B 17/1155; A61B 2017/00473; A61B 2017/07257
See application file for complete search history.

(56) References Cited

U.S. PATENT DOCUMENTS

| 5,205,459 A | 4/1993 | Brinkerhoff et al. |
| 5,718,360 A * | 2/1998 | Green .................. A61B 17/115 227/19 |

(Continued)

FOREIGN PATENT DOCUMENTS

JP    2017053394 A    3/2017

OTHER PUBLICATIONS

International Search Report dated May 19, 2020 and Written Opinion completed May 18, 2020 corresponding to counterpart Int'l Patent Application PCT/US2019/063930.

*Primary Examiner* — Eyamindae C Jallow
(74) *Attorney, Agent, or Firm* — Carter, DeLuca & Farrell, LLP

(57) ABSTRACT

Inserts and features to reduce or prevent spline crash in surgical staplers and/or to minimize damage resulting from spline crash in surgical staplers. An insert for a surgical stapler includes a body and spline covers. The body is configured to fit within a bore of a shell assembly and the spline covers extend inward from the body. Each of the spline covers are sized and dimensioned to cap a distal portion of splines of the shell assembly. A shell assembly for a surgical stapler includes shell splines that are disposed on an inner wall of an inner housing portion that defines a bore. The shell splines include a lead spline that has a leading end
(Continued)

positioned distal of a leading end of each of the other shell splines.

19 Claims, 15 Drawing Sheets

Related U.S. Application Data filed on Dec. 14, 2018, provisional application No. 62/779,736, filed on Dec. 14, 2018, provisional application No. 62/779,780, filed on Dec. 14, 2018, provisional application No. 62/779,718, filed on Dec. 14, 2018, provisional application No. 62/779,741, filed on Dec. 14, 2018.

(56) References Cited

U.S. PATENT DOCUMENTS

| | | |
|---|---|---|
| 7,857,187 B2 | 12/2010 | Milliman |
| 8,828,023 B2 | 9/2014 | Neff et al. |
| 9,833,235 B2 | 12/2017 | Penna et al. |
| 11,071,549 B2 * | 7/2021 | Wang ................. A61B 17/1155 |
| 11,497,501 B2 * | 11/2022 | Guerrera ............ A61B 17/1155 |
| 2012/0292373 A1 * | 11/2012 | Nalagatla ............ A61B 17/115 |
| | | 227/179.1 |
| 2016/0192934 A1 | 7/2016 | Williams et al. |
| 2016/0192938 A1 | 7/2016 | Sgroi, Jr. |
| 2016/0310141 A1 | 10/2016 | Penna et al. |
| 2017/0360443 A1 * | 12/2017 | Williams .......... A61B 17/1155 |
| 2018/0242974 A1 * | 8/2018 | Guerrera ............ A61B 17/1155 |
| 2019/0059901 A1 * | 2/2019 | Guerrera .......... A61B 17/00234 |
| 2019/0290284 A1 * | 9/2019 | Guerrera ............ A61B 17/1155 |

* cited by examiner

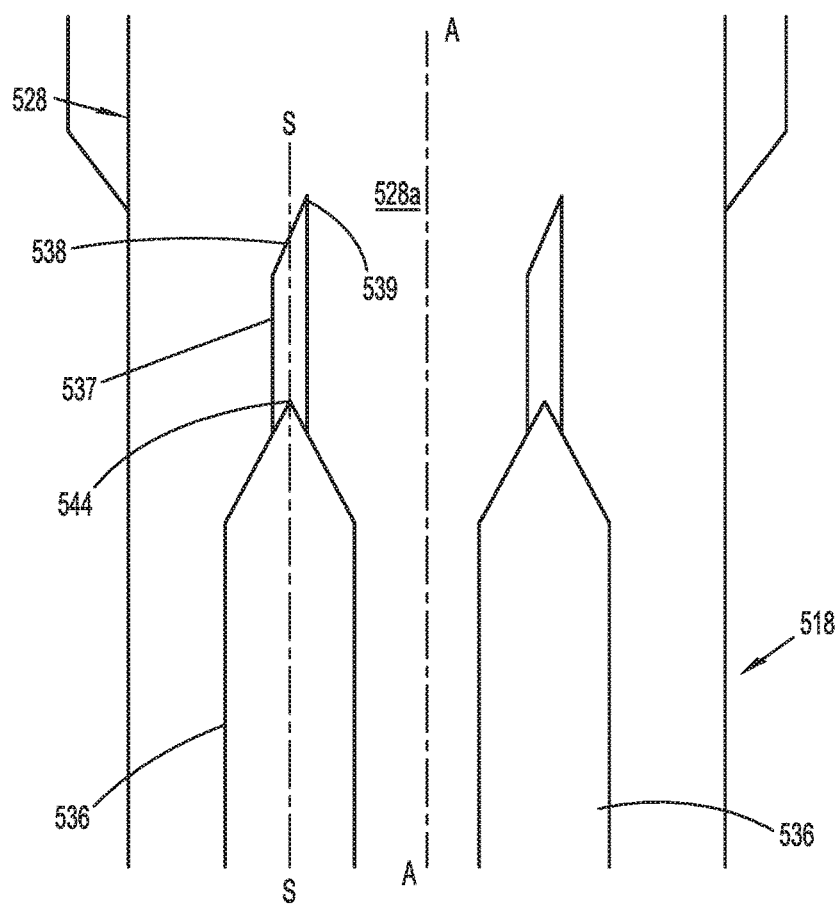
FIG. 16
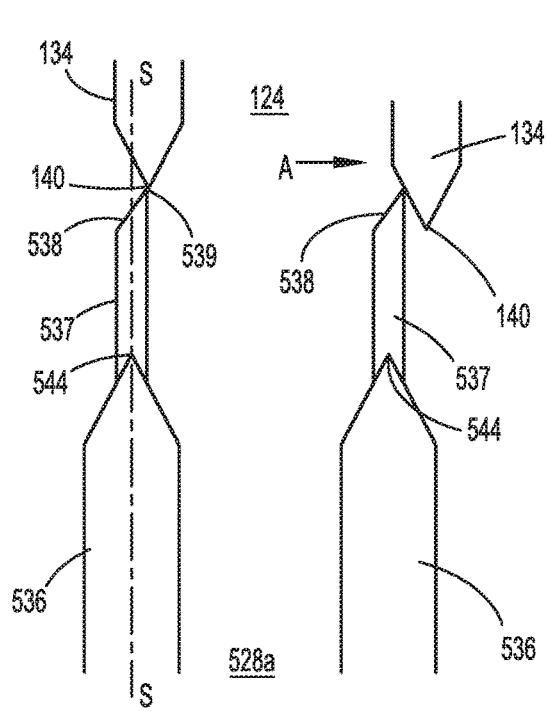 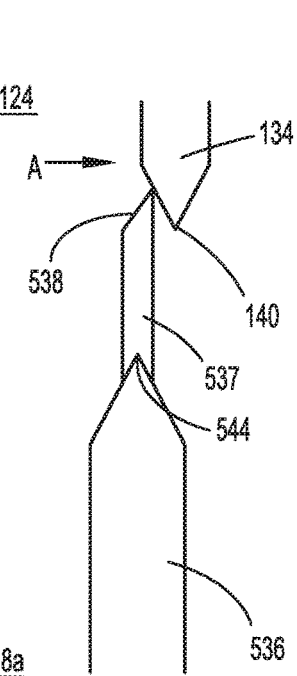 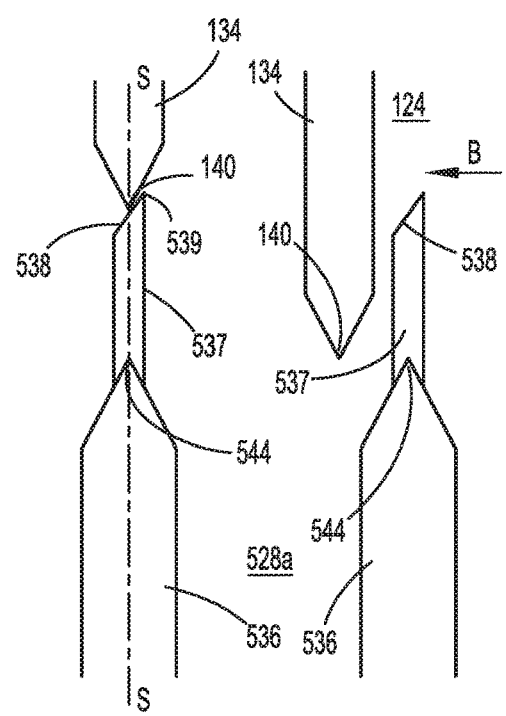
FIG. 17A   FIG. 17B   FIG. 18A   FIG. 18B

INSERTS, SPLINES, AND METHODS FOR REDUCING AND/OR ELIMINATING SPLINE CRASH IN SURGICAL INSTRUMENTS

CROSS-REFERENCE TO RELATED APPLICATIONS

The present application is a U.S. National Stage Application filed under 35 U.S.C. 371(a) of International Patent Application Serial No. PCT/US2019/063930, filed Dec. 2, 2019, which claims the benefit of and priority to U.S. Provisional Patent Application Ser. No. 62/779,718, filed on Dec. 14, 2018; U.S. Provisional Patent Application Ser. No. 62/779,727, filed on Dec. 14, 2018; U.S. Provisional Patent Application Ser. No. 62/779,736, filed on Dec. 14, 2018; U.S. Provisional Patent Application Ser. No. 62/779,741, filed on Dec. 14, 2018; U.S. Provisional Patent Application Ser. No. 62/779,759, filed on Dec. 14, 2018; and U.S. Provisional Patent Application Ser. No. 62/779,780, filed on Dec. 14, 2018, the entire content of each of which being incorporated herein by reference.

BACKGROUND

1. Technical Field

The present disclosure is directed to circular stapling devices, and more particularly, to circular stapling devices including structures to properly align an anvil assembly with a staple cartridge of a shell assembly of the circular stapling device.

2. Discussion of Related Art

Circular stapling devices are utilized by clinicians to apply one or more surgical fasteners, e.g., staples or two-part fasteners, to body tissue for the purpose of joining segments of body tissue together and/or for the creation of an anastomosis. Circular stapling devices generally include a cartridge or shell assembly supporting a plurality of annular rows of staples, an anvil assembly operatively associated with the cartridge assembly and having annular arrays of staple receiving pockets for providing a surface against which the plurality of annular rows of staples can be formed, and an annular blade for cutting tissue.

During a typical tissue fastening procedure, the anvil assembly of the stapling device is positioned within one segment of body tissue and the shell assembly and a body portion of the stapling device supporting the shell assembly are positioned in an adjacent segment of body tissue. The anvil assembly is then attached to the body portion of the stapling device and the stapling device is actuated to approximate the anvil assembly with a staple cartridge of the shell assembly and clamp the body tissue segments together.

Typically, the anvil assembly includes an anvil shaft that includes splines that mate with splines formed within a shell housing of the shell assembly to align the staple forming pockets of the anvil assembly with staple receiving pockets of the staple cartridge of the shell assembly. The splines on the anvil shaft and on the shell housing of the shell assembly include left and right tapered ends that define an apex. When the right tapered ends of the splines of the anvil assembly engage the left tapered ends of the shell assembly (or vice versa), the anvil assembly will be rotated to allow the splines of the anvil assembly to pass between the splines of shell assembly to align the anvil assembly with the shell assembly. However, if the right tapered end of one spline of the anvil assembly engages the right tapered end of one spline of the shell assembly and a left tapered end of another spline of the anvil assembly engages the left tapered end of another spline of the shell assembly, or if the apexes of the splines of the anvil assembly and the shell assembly simultaneously hit head on, e.g., crash, the splines of the anvil assembly and the shell assembly may be damaged and/or the anvil assembly and the shell assembly may bind such that approximation of the anvil and shell assemblies is prevented or malformation of the staples may occur during firing of the stapling device.

A continuing need exist for a circular stapling device including more reliable alignment structure for aligning the staple forming pockets of the anvil assembly with the staple receiving pockets of the staple cartridge of the shell assembly.

SUMMARY

This disclosure relates generally to inserts and features to reduce or prevent spline crash in surgical staplers and/or to minimize damage resulting from spline crash in surgical staplers.

In an aspect of the present disclosure, an insert for a surgical stapler includes a body and spline covers. The body is configured to fit within a bore of a shell assembly. The spline covers extend inward from the body and are each sized and dimensioned to cap a distal portion of splines of the shell assembly.

In aspects, the body is in the shape of a ring. The spline covers may be metal. Additionally, the insert may be monolithically formed.

In some aspects, each of the spline covers include a first camming wall and a second camming wall that form an apex at an intersection of the first and second camming walls. The body may include top and bottoms surfaces and one or more of the spline covers may extend below the bottom surface.

In another aspect of the present disclosure, a surgical stapler includes an anvil assembly, a shell assembly, and an insert. The anvil assembly includes an anvil shaft that has a plurality of anvil splines radially disposed about the anvil shaft. The shell assembly defines a bore about a central longitudinal axis of the shell assembly. The shell assembly includes a plurality of shell splines that are radially disposed on a wall that defines the bore such that the plurality of shell splines each extend into the bore. The insert is disposed within the bore and has a body and spline covers. Each of the spline covers extend inward from the body and are sized and dimensioned to cap a distal portion of a respective shell spline of the plurality of shell splines such that each of the plurality of shell splines is capped by a respective spline cover.

In aspects, the plurality of shell splines are made of plastic and each of the spline covers is made of metal.

In some aspects, the surgical stapler includes a handle assembly having an anvil retainer. The shell assembly is supported on a distal portion of the handle assembly. The anvil retainer is configured to pass through the bore of the shell assembly to engage and draw the anvil shaft through bore of the shell assembly. The plurality of anvil splines may be configured to engage the spline coves to clock the anvil assembly relative to the shell assembly such that each anvil spline of the plurality of anvil splines is disposed between adjacent shell splines of the plurality of shell splines.

In certain aspects, each shell spline of the plurality of shell splines includes first and second cam surfaces. Each of the spline covers may include first and second camming walls that are configured to cover the first and second cam surfaces, respectively. The first and second cam surfaces may be tapered at a first angle and the first and second camming wall may be tapered at a second angle which is less than the first angle.

In particular aspects, the shell assembly includes a staple cartridge which has a plurality of staples. The plurality of anvil splines may engage with the plurality of shell splines to radially align the anvil assembly with the shell assembly during firing of the plurality of staples.

In another aspect of the present disclosure, a method of stapling tissue includes positioning an insert within a bore of a shell assembly of a surgical stapler and drawing an anvil shaft of an anvil assembly into the bore of the shell assembly. The insert includes spline covers and the shell assembly includes shell splines that extend into the bore. Positioning the insert within the bore includes each spline cover capping a respective one of the shell splines. Drawing the anvil shaft into the bore includes an anvil spline disposed on an outer surface of the anvil shaft engaging one of the spline covers to clock the anvil assembly relative to the shell assembly.

In aspects, the method includes further drawing the anvil shaft into the bore of the shell assembly such that the anvil spline engages the shell splines to radially align the anvil assembly with the shell assembly. The anvil spline engaging one of the spline covers may coarsely clock the anvil assembly relative to the shell assembly and the anvil spline engaging the shell spline may finely clock the anvil assembly relative to the shell assembly.

In some aspects, the method includes securing the shell assembly to a distal portion of a handle assembly of a surgical stapler. The method may include extending an anvil retainer of the handle assembly distally through the bore of the shell assembly and coupling the anvil shaft to the anvil retainer. Drawing the anvil shaft into the bore may include actuating a knob of the handle assembly to draw the anvil shaft into the bore.

In another aspect of the present disclosure, an insert for a surgical stapler includes a body and a plurality of inert splines. The body is configured to fit within a bore of a shell assembly. The body is in the form of a ring and has inner and outer surfaces. The plurality of insert splines extend from the inner surface of the body. Each insert spline is configured to radially align with a shell spline of the shell assembly.

In aspects, the insert is made of metal. The insert may be monolithically formed.

In some aspects, the insert includes a rib that extends from the outer surface of the body. The rib may be configured to engage an inner surface of the shell assembly that defines the bore. The rib may protrude radially outward from the outer surface of the body a distance equal to one-half a thickness defined between the inner and outer surfaces of the body. The rib may extend along an outer surface of the body in a direction parallel to a longitudinal axis of the insert.

In particular aspects, the plurality of insert splines extend longitudinally from the body.

In another aspect of the present disclosure, a surgical stapler includes an anvil assembly, a shell assembly, and an insert. The anvil assembly includes an anvil shaft that has a plurality of anvil splines radially disposed thereabout. The shell assembly defines a bore about a central longitudinal axis thereof and includes a plurality of shell splines that are radially disposed on a wall that defines the bore such that each of the plurality of shell splines extends into the bore. The insert is disposed within the bore and has a body and a plurality of inset splines that extend inward from the body. The body has inner and outer surfaces. Each insert spline is aligned with a respective shell spline.

In aspects, the body is in the shape of a ring. The plurality of shell splines may be made of plastic and each of the insert splines may be made of metal.

In some aspects, the handle assembly includes an anvil retainer and the shell assembly is supported on a distal portion of the handle assembly. The anvil retainer may be configured to pass through the bore of the shell assembly and to engage and draw the anvil shaft through the bore of the shell assembly.

In particular aspects, the plurality of anvil splines is configured to engage the plurality of insert splines to clock the anvil assembly relative to the shell assembly such that each anvil spline is disposed between adjacent insert splines. The shell assembly may include a staple cartridge that has a plurality of staples. The plurality of anvil splines may be engaged with the plurality of shell splines to radially align the anvil assembly with the shell assembly during firing of the plurality of staples.

In certain aspects, the insert may include a rib that extends from the outer surface of the body. The rib may be configured to engage the wall of the shell assembly to radially fix the insert relative to the shell assembly. The shell assembly may include a feature such as a groove, slot, or notch in the wall defining the bore that receives the rib to fix the insert relative to the shell assembly.

In another aspect of the present disclosure, a method of stapling tissue includes positioning an insert within a bore of a shell assembly of a surgical stapler and drawing an anvil shaft of an anvil assembly into the bore of the shell assembly. The insert includes a plurality of insert splines and the shell assembly includes a plurality of shell splines that extends into the bore. Positioning the insert within the bore includes radially aligning each insert spline of the plurality of insert splines with a respective shell spline of the plurality of shell splines. Drawing the anvil shaft into the bore includes an anvil spline disposed on an outer surface of the anvil shaft engaging the plurality of insert splines to clock the anvil assembly relative to the shell assembly.

In aspects, the method includes further drawing the anvil shaft into the bore of the shell assembly such that the anvil spline engages the shell splines to radially align or clock the anvil assembly with the shell assembly. The anvil spline engaging the plurality of insert splines may coarsely clock the anvil assembly relative to the shell assembly and the anvil spline engaging the shell spline may finely clock the anvil assembly relative to the shell assembly.

In another aspect of the present disclosure, a method of stapling tissue includes positioning an insert within a bore of a shell assembly of a surgical stapler and drawing an anvil shaft of an anvil assembly into the bore of the shell assembly. The insert includes a plurality of insert splines and the shell assembly includes a plurality of shell splines that extend into the bore. Positioning the insert within the bore of the shell assembly. The insert includes a plurality of insert splines and the shell assembly includes a plurality of shell splines that extend into the bore. Positioning the insert within the bore includes radially aligning each insert spline of the plurality of the insert splines with a respective shell spline of the plurality of shell splines. Drawing the anvil shaft into the bore includes an anvil spline disposed on an outer surface of the anvil shaft engaging the plurality of insert splines to clock the anvil assembly relative to the shell assembly.

In aspects, the method includes further drawing the anvil shaft into the bore of the shell assembly such that the anvil spline engages the shell spline to clock the anvil assembly with the shell assembly. The anvil spline may engage the plurality of insert splines to coarsely clock the anvil assembly relative to the shell assembly and the anvil spline may engage the shell spline to finely clock the anvil assembly relative to the shell assembly.

In some aspects, the method includes securing the shell assembly to a distal portion of a handle assembly of a surgical stapler. The method may include extending an anvil retainer of the handle assembly distally through the bore of the shell assembly and coupling the anvil shaft to the anvil retainer. Drawing the anvil shaft into the bore may include actuating a knob of the handle assembly to draw the anvil shaft into the bore.

In another aspect of the present disclosure, a shell assembly for a surgical stapler includes a housing portion, an inner housing portion, and shell splines. The housing portion is configured to support an annular staple cartridge. The inner housing portion defines a longitudinal axis of the shell assembly and includes a bore defined about the longitudinal axis. The shell splines are disposed on an inner wall of the inner housing portion that defines the bore. The shell splines include a lead spline that has a leading end positioned distal of a leading end of each of the other shell splines.

In aspects, the position of a leading end of one of the other shell splines is offset along the longitudinal axis relative to leading ends of the remaining shell splines and the lead spline.

In some aspects, the shell splines include the lead spline, a second shell spline, and a third shell spline. A leading end of the second shell spline may be longitudinally positioned between the leading end of the lead spline and a leading end of the third shell spline. The shell splines may include a fourth shell spline. The leading end of the third shell spline may be longitudinally positioned between the leading end of the second shell spline and a leading end of the fourth shell spline.

In another aspect of the present disclosure, a surgical stapler includes an anvil assembly and a shell assembly. The anvil assembly includes an anvil shaft that has anvil splines radially disposed thereabout. The shell assembly is configured to support an annular staple cartridge. The shell assembly includes an inner housing portion that defines a longitudinal axis of the shell assembly and includes a bore defined about the longitudinal axis. The shell splines are disposed on an inner wall of the inner housing portion defining the bore. The shell splines include a lead spline that has a leading end positioned distal of a leading end of each of the other shell splines.

In aspects, the surgical stapler includes a handle assembly that has an anvil retainer. The shell assembly may be supported on a distal portion of the handle assembly. The anvil retainer may be configured to pass through the bore of the shell assembly to engage and draw the anvil shaft through the bore of the shell assembly. The leading end of the lead spline may be configured to engage one of the anvil splines before the leading ends of the other shell splines engage anvil splines to clock the anvil shaft relative to the shell assembly.

In another aspect of the present disclosure, a method of stapling tissue includes drawing an anvil shaft of an anvil assembly into a bore of a shell assembly and firing a plurality of staples from a staple cartridge supported by the shell assembly. Drawing the anvil shaft into the bore includes an anvil spline disposed on an outer surface of the anvil shaft engaging a leading end of a lead spline of the shell assembly positioned on an inner wall that defines the bore to clock the anvil assembly relative to the shell assembly. The leading end of the lead spline is longitudinally positioned distal to leading ends of other shell splines of the shell assembly positioned on the inner wall that defines the bore. Firing the plurality of staples includes firing the plurality of staples towards an anvil of the anvil assembly after drawing the anvil shaft into the bore.

In aspects, the method includes further drawing the anvil shaft into the bore such that addition anvil splines disposed on an outer surface of the anvil shaft engage leading ends of the other shell splines subsequent to the leading end of the lead spline engaging the anvil spline. The anvil spline may engage the leading end of the lead spline to coarsely clock the anvil assembly relative to the shell assembly and the additional anvil splines engaging the leading ends of the other shell splines may finely clock the anvil assembly relative to the shell assembly.

In some aspects, the method includes securing the shell assembly to a distal portion of a handle assembly of a surgical stapler. The method may include extending an anvil retainer of the handle assembly distally through the bore of the shell assembly and coupling the anvil shaft to the anvil retainer. Drawing the anvil shaft into the bore may include actuating a knob of the handle assembly to draw the anvil shaft into the bore.

In another aspect of the present disclosure, a shell assembly for a surgical stapler includes a housing portion, an inner housing portion, shell splines, and a flexible tine. The housing portion is configured to support an annular staple cartridge. The inner housing portion defines a longitudinal axis of the shell assembly and includes an inner wall that defines a bore about the longitudinal axis. The shell splines are disposed on an inner wall of the inner housing portion that defines the bore. Each of the shell splines has a distal leading end. The flexible tine extends distally from one of the shell splines such that the flexible tine is positioned distal of the distal leading ends of the shell splines.

In aspects, the distal leading ends of the shell splines are longitudinally aligned with one another. The flexible tine may extend distally from an apex of the one of the shell splines. The flexible tine may be spaced apart from the inner wall to define a gap therebetween. The flexible tine may not be directly attached to the inner wall.

In some aspects, the flexible tine is configured to deflect in a direction transverse to the longitudinal axis. A distal end of the flexible tine may be blunt. The flexible tine may have a width less than or equal to one half a width of the one of the shell splines.

In another aspect of the present disclosure, a surgical stapler includes a handle, an anvil assembly, and a shell assembly. The handle assembly has an anvil retainer. The anvil assembly includes an anvil shaft that has anvil splines radially disposed about the anvil shaft. The anvil shaft is releasably coupled to the anvil retainer. The shell assembly is secured to a distal portion of the handle assembly. The shell assembly includes a housing portion, an inner housing portion, shell splines, and a flexible tine. The housing portion is configured to support an annular staple cartridge. The inner housing portion defines a longitudinal axis of the shell assembly and includes an inner wall that defines a bore about the longitudinal axis. The shell splines are disposed on an inner wall of the inner housing portion that defines the bore. Each of the shell splines has a distal leading end. The flexible tine extends distally from one of the shell splines such that the flexible tine is positioned distal of the distal leading ends of the shell splines. The flexible tine is configured to engage one of the anvil splines as the handle assembly draws the anvil shaft through the bore.

In aspects, the flexible tine is configured to coarsely clock the anvil shaft relative to the shell assembly as the handle draws the anvil shaft through the bore. The shell splines may be configured to engage the anvil splines to finely clock the anvil shaft relative to the shell assembly subsequent to the flexible tine engaging the one of the anvil splines.

In another aspect of the present disclosure, a method of stapling tissue includes drawing an anvil shaft of an anvil assembly into a bore of a shell assembly and firing a plurality of staples from a staple cartridge supported by the shell assembly. Drawing the anvil shaft into the bore includes an anvil spline disposed on an outer surface of the anvil shaft engaging a flexible that extends from one of a plurality of shell splines of the shell assembly positioned on an inner wall that defines the bore to coarsely clock the anvil assembly relative to the shell assembly. The flexible spline is longitudinally positioned distal to leading ends of each of the plurality of shell splines positioned on the inner wall that defines the bore. Firing the plurality of staples includes firing the plurality of staples towards an anvil of the anvil assembly after drawing the anvil shaft into the bore.

In aspects, the method includes further drawing the anvil shaft into the bore such that the anvil spline engages one or more of the plurality of shell splines to finely clock the anvil assembly relative to the shell assembly subsequent to coarsely clocking the anvil assembly relative to the shell assembly.

In some aspects, the anvil spline engaging the flexible tine deflects the flexible tine in a direction transverse to a longitudinal axis of the shell assembly.

In particular aspects, the method includes securing the shell assembly to a distal portion of a handle assembly of a surgical stapler. The method may include extending an anvil retainer of the handle assembly distally through the bore of the shell assembly and coupling the anvil shaft to the anvil retainer. Drawing the anvil shaft into the bore may include actuating a knob of the handle assembly to draw the anvil shaft into the bore.

In another aspect of the present disclosure, a shell assembly for a surgical stapler includes a housing portion, an inner housing portion, shell splines, and a first tine. The housing portion is configured to support an annular staple cartridge. The inner housing portion defines a longitudinal axis of the shell assembly and includes an inner wall that defines a bore about the longitudinal axis. The shell splines are disposed on the inner wall with each of the shell splines having a distal leading end. The first tine extends distally from one of the shell splines. The first tine has a leading portion positioned distal of the distal leading ends of the shell splines. The leading portion having a biased leading edge.

In aspects, the one of the shell splines defines a shell axis that is parallel to the longitudinal axis and extends through an apex of the one of the shell splines. A leading portion of the first tine may be offset from the shell axis. The first tine may be secured to the inner wall of the inner housing portion.

In some aspects, the shell assembly includes a second tine that extends distally from another shell spline. The second tine may have a leading portion that has a biased leading edge. The biased leading edge of the first tine may be biased in the same direction as the biased leading edge of the second tine. The second tine may have a leading point that is longitudinally offset from the leading point of the first tine.

In another aspect of the present disclosure, a surgical stapler includes a handle assembly, an anvil assembly, and a shell assembly. The handle assembly has an anvil retainer. The anvil assembly includes an anvil shaft that has anvil splines radially disposed thereabout. The anvil shaft is releasably coupled to the anvil retainer. The shell assembly is secured to a distal portion of the handle assembly and includes a housing portion, an inner housing portion, shell splines, and a first tine. The housing portion is configured to support an annular staple cartridge. The inner housing portion defines a longitudinal axis of the shell assembly and includes an inner wall that defines a bore about the longitudinal axis. The shell splines are disposed on the inner wall of the inner housing portion and each have a distal leading end. The first tine extends distally from one of the shell splines. The first tine has a leading portion that is positioned distal of the distal leading ends of the shell splines. The leading portion has a biased leading edge and is configured to engage one of the anvil splines as the handle assembly draws the anvil shaft through the bore.

In aspects, the first tine is configured to coarsely clock the anvil shaft relative to the shell assembly as the handle assembly draws the anvil shaft through the bore. The shell splines may be configured to engage the anvil splines to finely clock the anvil shaft relative to the shell assembly subsequent to the first tine engaging the one of the anvil splines.

In another aspect of the present disclosure, a method of stapling tissue includes drawing an anvil shaft of an anvil assembly into a bore of a shell assembly and firing a plurality of staples from a staple cartridge supported by the shell assembly towards an anvil of the anvil assembly after drawing the anvil shaft into the bore. Drawing the anvil shaft into the bore includes an anvil spline disposed on an outer surface of the anvil shaft engaging a first tine that extends from one of a plurality of shell splines of the shell assembly positioned on an inner wall that defines the bore to coarsely clock the anvil assembly relative to the shell assembly. The first spline is longitudinally positioned distal to leading ends of each of the plurality of shell splines positioned on the inner wall.

In aspects, the method includes further drawing the anvil shaft into the bore such that the anvil spline engages one or more of the plurality of shell splines to finely clock the anvil assembly relative to the shell assembly subsequent to coarsely clocking the anvil assembly relative to the shell assembly.

In some aspects, the method includes securing the shell assembly to a distal portion of a handle assembly of a surgical stapler. The method may include extending an anvil retainer of the handle assembly distally through the bore of the shell assembly and coupling the anvil shaft to the anvil retainer. Drawing the anvil shaft into the bore may include actuating a knob of the handle assembly to draw the anvil shaft into the bore.

In another aspect of the present disclosure, an anvil assembly for a circular stapler includes an anvil head and an anvil shaft. The anvil shaft has a distal portion that is coupled to the anvil head and defines a longitudinal axis. The anvil shaft includes a boss and a first anvil spline that protrudes from an outer surface of the anvil shaft. The first anvil spline extends along the outer surface of the anvil shaft in a direction parallel to the longitudinal axis. The first spline has a spline contact surface are configured to engage a shell assembly to radially cock the anvil assembly with the shell assembly. The first spline defines a relief cutout which reduces the spline contact surface area of the first anvil spline. The boss is disposed about the anvil shaft and is toroidal in shape. The boss has an outer surface with relief cutouts that are defined in the outer surface of to reduce a boss contact surface area of the boss. The boss contact surface area is configured to engage the shell assembly to align the anvil assembly with the shell assembly.

In aspects, the first anvil spline includes a leading portion and a trailing portion. The relief cutout may be defined between the leading and trailing portions. The relief cutout may reduce an extent that the anvil spline protrudes from the outer surface of the anvil shaft between the leading and trailing portions. The relief cutout may reduce a width of the anvil spline between the leading and trailing portions.

In some aspects, the anvil shaft is pivotally coupled to the anvil head. The boss may be positioned on the anvil shaft between the first anvil spline and the anvil head. The boss may be positioned on the anvil shaft between the first anvil spline and the anvil head.

In certain aspects, the anvil shaft includes a second anvil spline protruding from the outer surface of the anvil shaft. The second anvil spline may be radially spaced about the outer surface from the first anvil spline. The second anvil spline may be longitudinally aligned with the first anvil spline.

In another aspect of the present disclosure, a circular stapling device includes a handle assembly, a shell assembly, and an anvil assembly. The handle assembly has an anvil retainer. The shell assembly is secured to a distal portion of the handle assembly and has an inner housing portion that includes an inner wall which defines a bore that extends through the shell assembly. The inner wall includes shell splines that extend from the inner wall into the bore. The anvil assembly includes an anvil head and an anvil shaft. The anvil shaft defines a longitudinal axis and has a distal portion that is coupled to the anvil head. The anvil shaft includes a boss and a first anvil spline that protrudes from an outer surface of the anvil shaft. The first anvil spline extends along the outer surface of the anvil shaft in a direction parallel to the longitudinal axis. The first anvil spline has a spline contact surface area that is configured to engage one or more of the shell splines to clock the anvil assembly with the shell assembly. The first anvil spline defines a relief cutout which reduces the spline contact area of the first anvil spline. The boss is disposed about the anvil shaft and is toroidal in shape. The boss has an outer surface with relief cutouts that are defined in the outer surface to reduce a boss contact surface area of the boss. The boss contact surface area is configured to engage the shell assembly to align the anvil assembly with the shell assembly. The anvil retainer is configured to extend through the bore of the shell assembly and to be received within the anvil shaft to approximate the anvil assembly relative to the shell assembly.

In aspects, the first anvil spline is configured to engage one or more of the shell splines when the boss is engaged with the shell assembly. The boss may be configured to engage the inner wall of the shell assembly to coaxially align the anvil shaft with the shell assembly.

In another aspect of the present disclosure, a method of stapling tissue includes drawing an anvil shaft of an anvil assembly through a bore of a shell assembly such that an anvil spline which protrudes from an outer surface of the anvil shaft engages a shell spline of the shell assembly which extends into the bore to clock the anvil assembly relative to the shell splines. The anvil spline has a relief cutout that is defined by reducing a contact surface area which contacts the shell splines. The method also includes further drawing the anvil shaft through the bore such that a boss is defined about the anvil shaft engages an inner wall of the shell assembly which defines the bore to coaxially align the anvil shaft with the bore. The boss has an outer surface which defines relief pockets. The relief pockets reduce a boss contact surface area of the boss with the inner wall of the shell assembly.

In aspects, where further drawing the anvil shaft through the bore includes the boss engaging the inner wall to maintain engagement between the anvil spline and the at least one shell spline.

In some aspect, the method includes securing the shell assembly to a distal portion of a handle assembly of a surgical stapler. The method may include extending an anvil retainer of the handle assembly distally through the bore of the shell assembly and coupling the anvil shaft to the anvil retainer. Drawing the anvil shaft into the bore may include actuation a knob of the handle assembly to draw the anvil shaft into the bore.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 16 is a schematic side view of an exemplary embodiment of a shell spline configuration of another shell assembly provided in accordance with the present disclosure having one or more biased tines;

FIGS. 17A and 17B are schematic views of the shell spline configuration of the shell assembly of FIG. 16;

FIGS. 18A and 18B are schematic views of the shell spline configuration of the shell assembly of FIG. 16;

DETAILED DESCRIPTION

Figure 1:
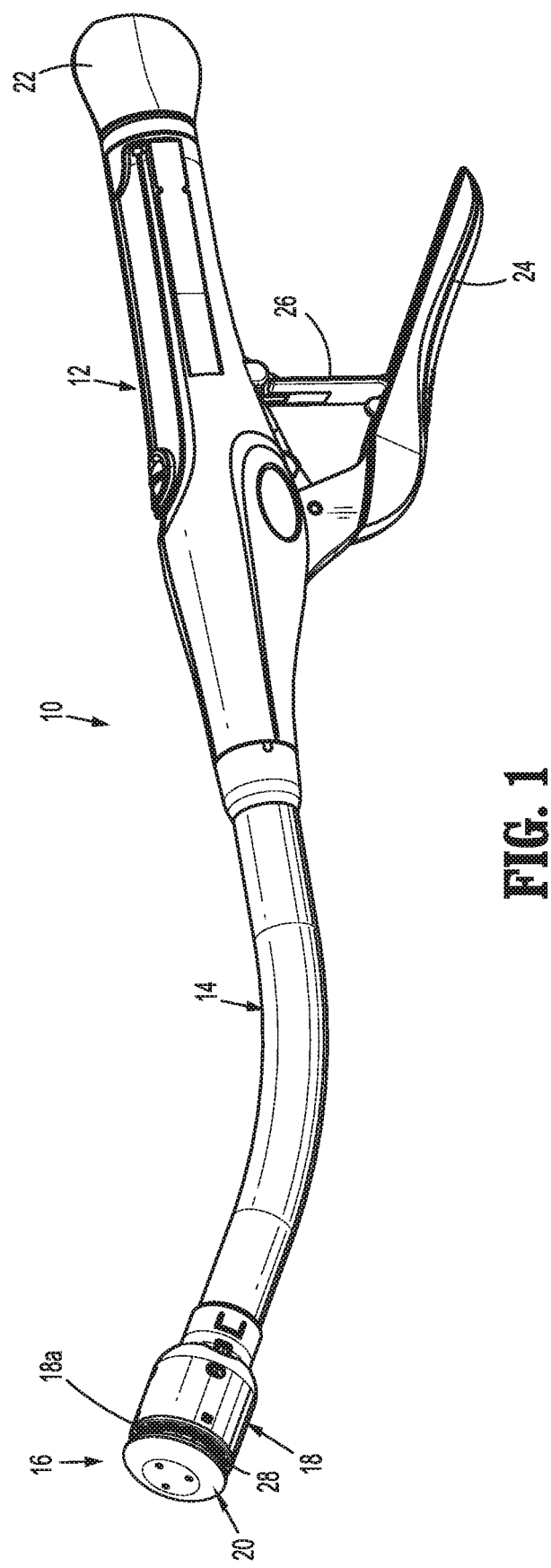
FIG. 1 is a side perspective view of an exemplary embodiment of the presently disclosed surgical stapling device with a tool assembly in a clamped position.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. In addition, the term "endoscopic" is used generally to refer to endoscopic, laparoscopic, arthroscopic, and/or any other procedure conducted through small diameter incision or cannula.

Figure 2:
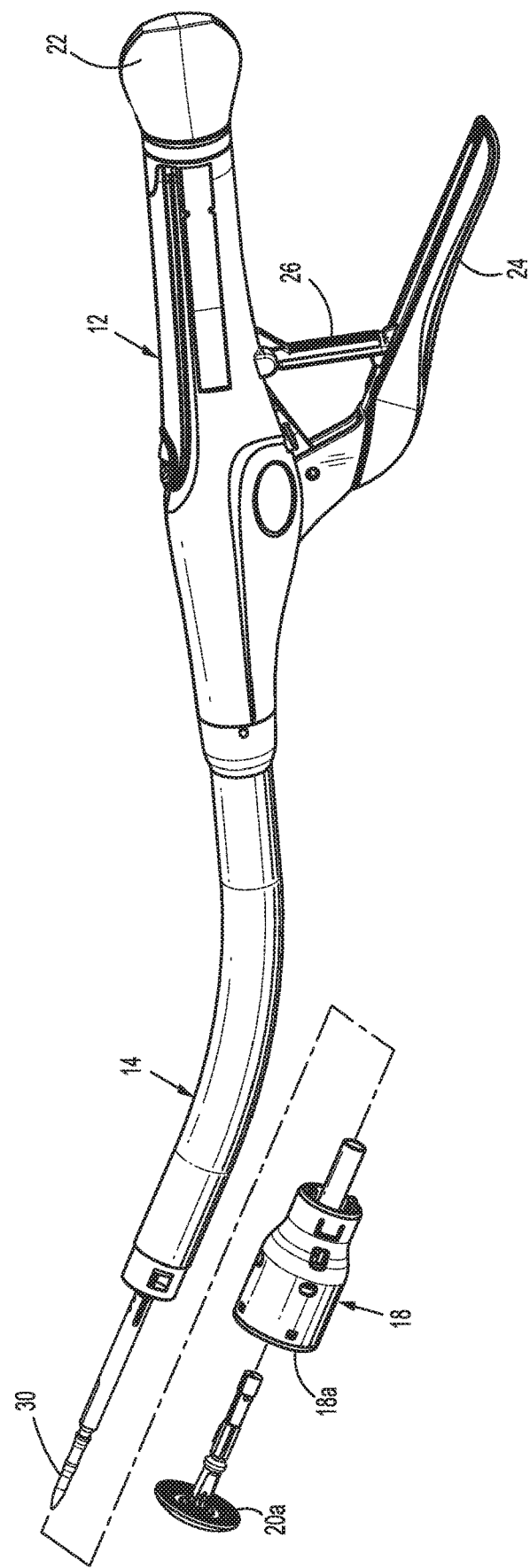
FIG. 2 is a side perspective view of the surgical stapling device shown in FIG. 1 with a shell assembly of the tool assembly and an anvil assembly of the tool assembly separated from the remaining portion of the stapling device.

Referring to FIGS. 1 and 2, the presently disclosed surgical stapling device shown generally as 10 includes a handle assembly 12, an elongated body portion 14 that extends distally from the handle assembly 12, and a tool assembly 16 that is supported on a distal portion of the elongated body portion 14. The tool assembly 16 includes a cartridge or shell assembly 18 that supports a staple cartridge 18a and an anvil assembly 20 that supports an anvil 20a. The handle assembly 12 includes an approximation knob 22 that operates an approximation mechanism (not shown) to move the anvil assembly 20 between unclamped and clamped positions in relation to the cartridge assembly 18, a firing trigger 24 that that operates a firing mechanism (not shown) to fire staples (not shown) from the staple cartridge 18a into tissue, and a firing trigger lockout 26 that is pivotally supported on the handle assembly 12 and is positioned to prevent inadvertent firing of the stapling device 10. For a detailed description of an exemplary circular stapling device including known approximation, firing, and lockout mechanisms reference can be made to U.S. Pat. No. 7,857,187 ("the '187 Patent"), the entire contents of which are hereby incorporated by reference.

Although the presently disclosed stapling device 10 is shown and described as being a manually powered device, it is envisioned that the stapling device 10 can be an electrically powered device such as described in U.S. Pat. No. 9,833,235 ("the '235 Patent"), the entire contents of which are hereby incorporated by reference. In addition, it is contemplated that the stapling device 10 can be used with a surgical robot such as describe in U.S. Pat. No. 8,828,023 ("the '023 Patent"), the entire contents of which are hereby incorporated by reference.

The staple cartridge 18a of the shell assembly 18 and the anvil 20a of the anvil assembly 20, have an annular configuration. The anvil assembly 20 is movable in relation to the shell assembly 18 from a spaced position to a clamped position to move the anvil 20a into juxtaposed alignment with the staple cartridge 18a. The staple cartridge 18a defines staple receiving slots 28 that are aligned with staple deforming recesses (not shown) of the anvil 20a when the staple cartridge 18a and the anvil 20a are properly aligned such that staples ejected from the staple receiving slots 28 are deformed within the staple receiving recesses when the stapling device 10 is fired.

The anvil assembly 20 is supported on an anvil retainer 30 (FIG. 2) which forms part of the approximation mechanism (not shown) of the stapling device 10. The anvil retainer 30 is configured to releasably engage the anvil assembly 20. The anvil retainer 30 includes a distal portion and a proximal portion. The distal portion of the anvil retainer 30 extends from a distal end of the elongate body portion 14 of the stapling device 10 and through the shell assembly 18 to a position to engage the anvil assembly 20. The proximal portion of the anvil retainer 30 is operatively connected to the approximation knob 22 such that rotation of the approximation knob 22 causes the anvil retainer 30 to move within the shell assembly 18 to move the anvil assembly 20 in relation to the staple cartridge 18a between the spaced position and the clamped position. The shell assembly 18 includes an annular knife (not shown) that is movable from a retracted position to an advanced position within the shell assembly 18 during firing of the stapling device 10 to transect tissue clamped between the staple cartridge 18a and the anvil 20a.

Referring to FIG. 2, the shell assembly 18 is releasably coupled to a distal portion of the elongated body 14 of the stapling device 10 to facilitate replacement of the shell assembly 18 after each firing of the stapling device 10. Examples of mechanisms for releasably coupling the shell assembly 18 to the elongate body portion 14 of the stapling device 10 are described in U.S. Patent Publication Nos. 2016/0310141, 2016/0192938, and 2016/0192934. The entire disclosure of each of these publications is hereby incorporated by reference.

Figure 3:
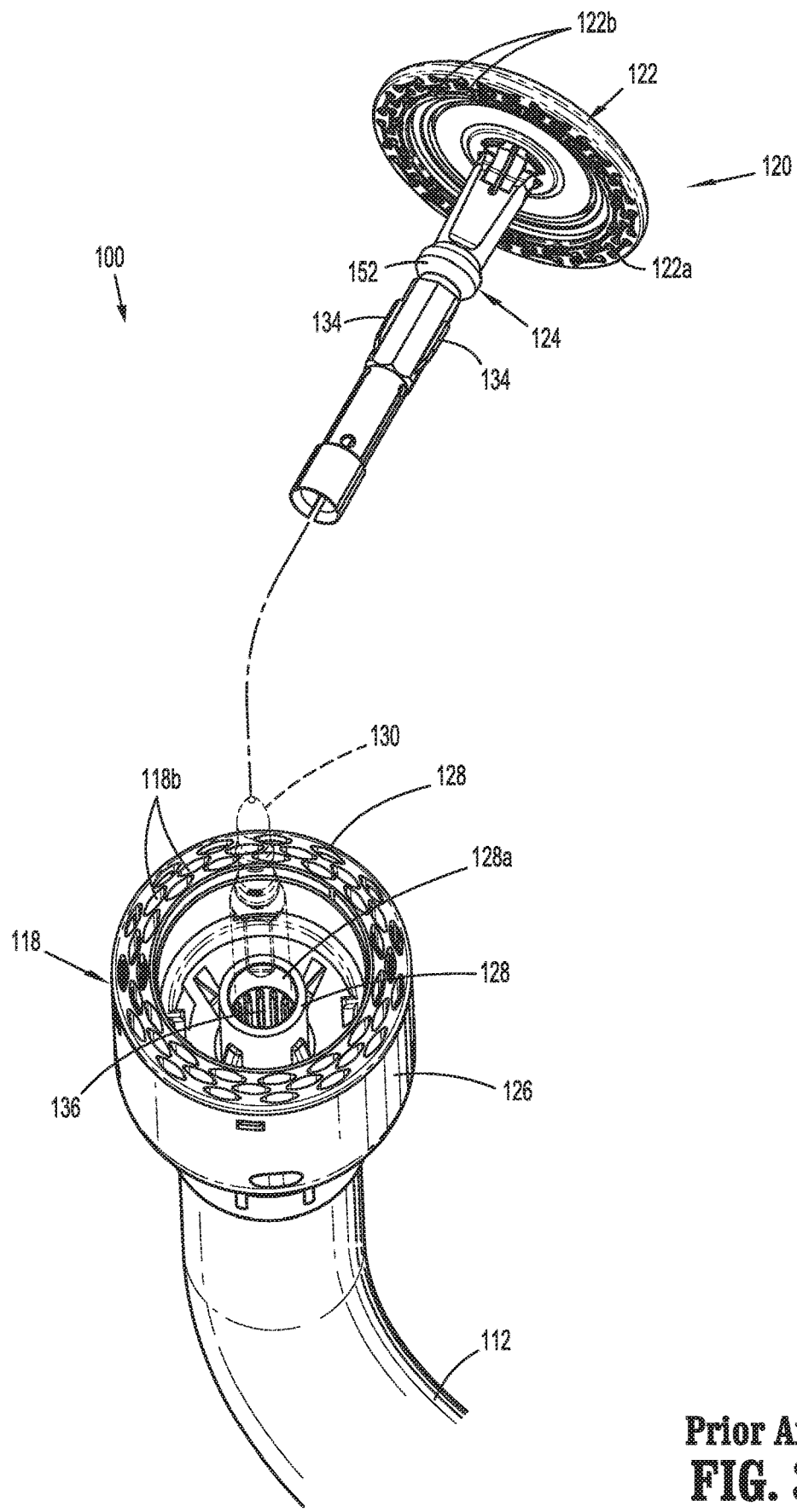
FIG. 3 is a perspective view from a distal end of a "Prior Art" surgical stapling device with the anvil assembly of the tool assembly of the surgical stapling device separated from an anvil retainer (shown in phantom) of the surgical stapling device.

Referring to FIG. 3, in "Prior Art" circular stapling devices 100, an anvil assembly 120 includes an anvil head 122 and an anvil shaft 124, and a shell assembly 118 includes a staple cartridge 118a and a shell housing 126 having an inner housing portion 128 that defines a through bore 128a. The anvil head 122 supports an anvil 122a that defines annular arrays of staple deforming recesses 122b and the staple cartridge 118a defines annular arrays of staple receiving slots 118b. An anvil retainer 130 (shown in phantom) includes a distal end that is configured to releasably engage the anvil shaft 124 of the anvil assembly 120. The anvil retainer 130 is received within the through bore 128a and is movable between retracted and advanced positions. When the anvil shaft 124 is coupled to the anvil retainer 130 and the anvil retainer 130 is retracted (via actuation of the approximation knob 22, FIG. 1), the anvil shaft 124 is drawn into the through bore 128a of the inner housing portion 128 of the shell housing 126.

In order to align the arrays of staple deforming recesses 122b of the anvil head 122 of the anvil assembly 120 with the staple receiving slots 118b of the staple cartridge 118a of the shell assembly 118, the anvil shaft 124 includes a plurality of anvil splines 134 including adjacent anvil splines 134a, 134b (FIG. 4) that are received within guide channels defined between adjacent shell splines 136 formed along an inner wall of the inner housing portion 128 of the shell housing 126. Each of the anvil splines 134 of the anvil assembly 120 defines a central axis "Z" and left and right tapered cam surfaces 138a, 138b positioned on opposite sides of the central axis "Z" as viewed in FIG. 4. The tapered surfaces 138a, 138b meet at their proximal ends at an apex 140. Similarly, each of the shell splines 136 of the shell assembly 118 defines a central axis "X" and left and right tapered cam surfaces 142a, 142b positioned on opposite sides of the central axis "X". The tapered surfaces 142a, 142b meet at their distal ends at an apex 144.

When the anvil assembly 120 is attached to the anvil retainer 130 and the anvil retainer 130 and anvil assembly 120 are retracted into the through bore 128a (FIG. 3) of the inner housing portion 128 of the shell housing 126, the anvil splines 134 of the anvil assembly 120 move towards the shell splines 136 of the shell assembly 118. If the anvil splines 134 are misaligned with channels 148 defined between the shell splines 136 of the shell assembly 118, the apexes 140 of the anvil splines 134a, 134b will engage one of the cam surfaces 142a, 142b of the shell splines 136 to rotate or "clock" the anvil assembly 120 relative to the shell assembly 118. When all of the apexes 140 of all of the anvil splines 134a, 134b (only two are shown) engage the left tapered cam surface 142a of the shell splines 136, the engagement urges or cams the anvil assembly 120 to rotate in the direction indicated by arrow "S" to realign the anvil splines 134a, 134b so that they enter into the channels 148 defined between the shell splines 136 of the shell assembly 118. Similarly, when all of the apexes 140 of all of the anvil splines 134a, 134b engage the right tapered cam surface 142b of the shell splines 136, the engagement urges or cams the anvil assembly 120 to rotate in the direction indicated by arrow "T" to clock the anvil shaft 124 to realign the anvil splines 134a, 134b so that they enter into the channels 148 defined between the shell splines 136 of the shell assembly 118. However, if the apexes 140 of any two of the anvil splines 134a, 134b simultaneously engage the left and right tapered cam surfaces 142a, 142b of the two shell splines 136 of the shell assembly 118, the engagement simultaneously urges or cams the anvil assembly 120 in opposite directions. When this happens, the anvil splines 134a, 134b and shell splines 136 will bind until one or both of the anvil splines 134 and/or the shell splines 136 fractures. In addition, if the apexes 140 of the anvil splines 134a, 134b are aligned with the apexes 144 of the shell splines 136, the apexes may crash into each other causing damage to the anvil splines 134a, 134b and/or the shell splines 136. When the anvil splines 134 and 136 crash into or bind with each other and proper alignment between staple receiving recesses 127 of the anvil assembly 120 and staple receiving slots 128 of the shell assembly 118 is not achieved, improper staple formation or locking of the stapling device 100 may result.

Figure 6:
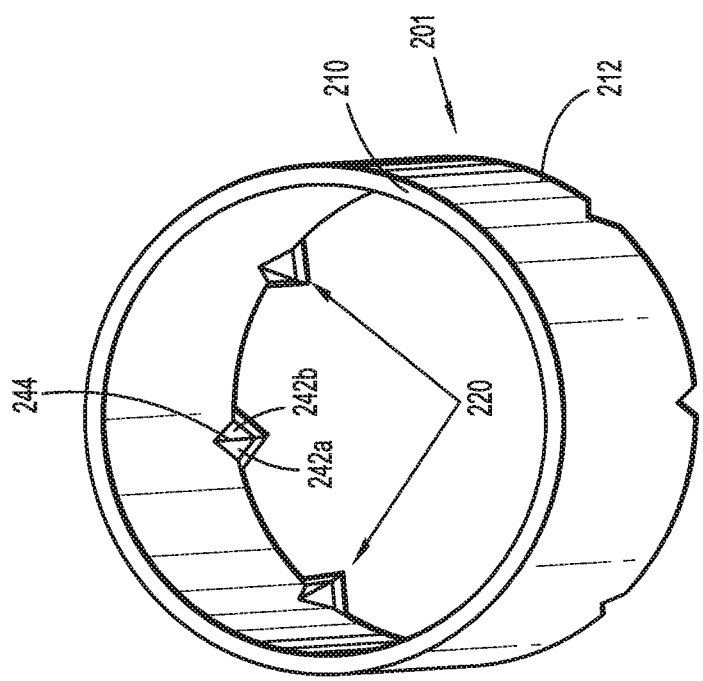
FIG. 6 is another perspective view of the insert of FIG. 5.
Figure 5:
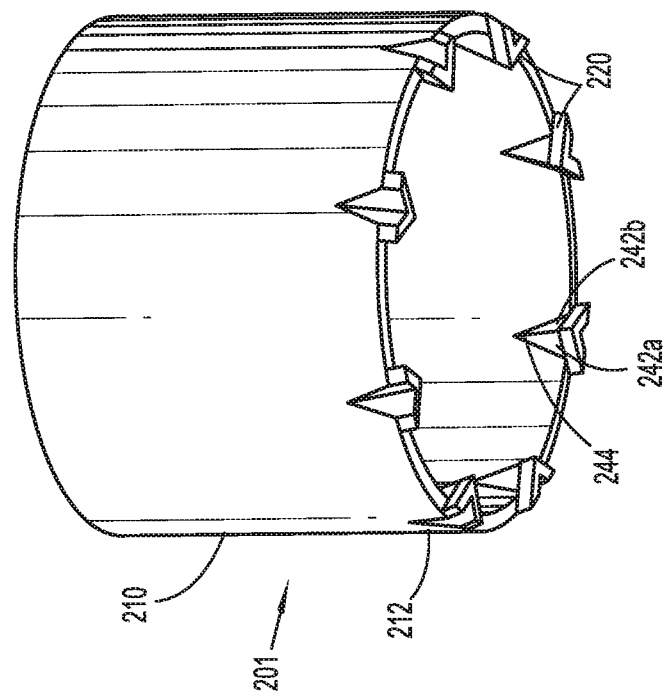
FIG. 5 is a perspective view of an exemplary embodiment of an insert for use with the shell assembly of the surgical stapling device of FIG. 1 and/or the shell assembly of the "Prior Art" surgical stapling device of FIG. 3.
Figure 7:
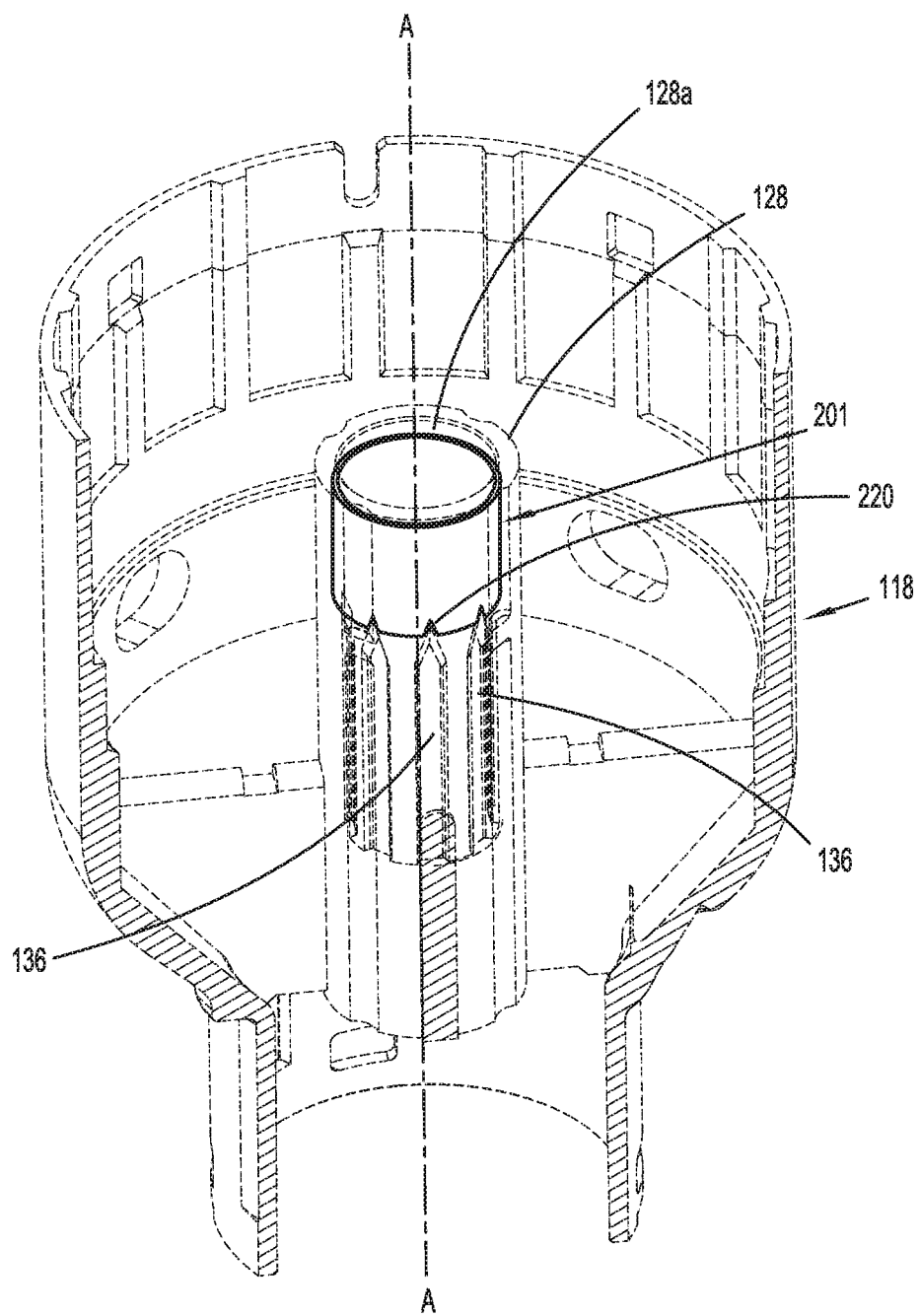
FIG. 7 is a perspective cutaway view of the shell assembly of the "Prior Art" surgical stapling device of FIG. 3 with the insert of FIG. 5 installed within a bore of the shell assembly.

Referring now to FIGS. 5-7, an insert 201 is provided in accordance with the present disclosure. The insert 201 is configured to be installed within the bore 128a of the shell assembly 118 to clock the anvil assembly 120 (FIG. 3) into alignment with the shell assembly 118. The insert 201 is configured to protect the shell splines 136 from damage. Specifically, the insert 201 is formed of a metal, e.g., steel, and the shell splines 136 and the anvil splines 134 are generally formed of plastic such that the insert 201 is substantially stronger than the anvil splines 134. In addition, the insert 201 is configured to retrofit existing shell assemblies 118 to enhance the clocking and/or to protect the shell splines 136 from damage. The insert 201 may be installed or positioned within the bore 128a of the shell assembly 118 before a surgical procedure. The insert 201 may be positioned by the manufacturer of the shell assembly 118 or may be positioned by a clinician before a surgical procedure.

The insert 201 has a body 210 in the form of a ring. The body 210 is sized and dimensioned to be received within the bore 128a such that the body 210 engages walls defining the bore 128a. When the insert 201 is installed in the bore 128a, a longitudinal axis of the insert 201 is coincident with the longitudinal axis A-A of the shell assembly 118. The body 210 may frictionally engage the walls defining the bore 128a to secure the body 210 within the bore 128a. Additionally or alternatively, the body 210 may be slightly larger than the bore 128a such that the insert 201 must be press-fit into the bore 128a. The body 210 has a bottom portion 212 that includes spline covers 220. Each of the spline covers 220 is formed of metal and the body 210 may be formed of plastic or metal. The body 210 and the spline covers 220 may be monolithically formed. Alternatively, the body and the spline covers 220 may form a unitary unit with one another.

Figure 4:
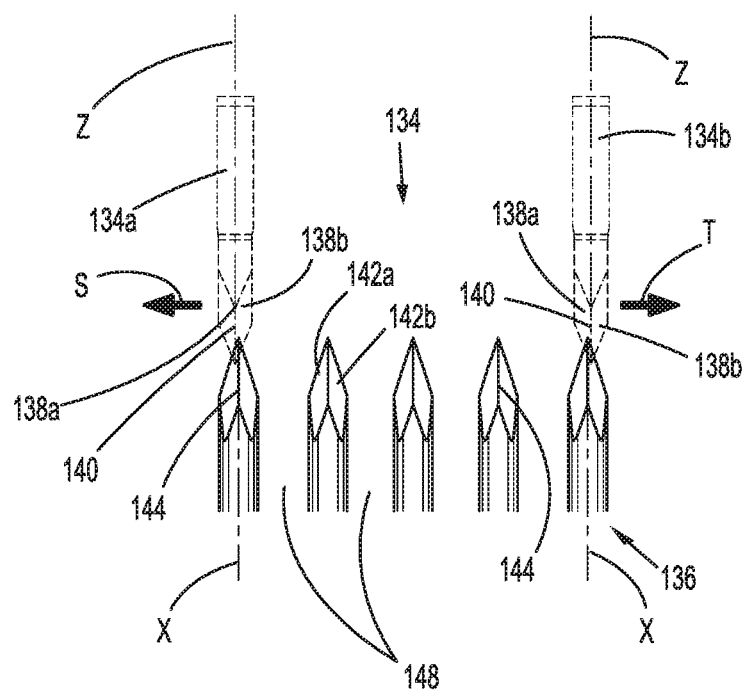
FIG. 4 is a schematic view of a spline configuration of the anvil assembly of the "Prior Art" surgical stapling device shown in FIG. 3.

Each spline cover 220 is configured to cover or cap the cam surfaces 142a, 142b of one of the shell splines 136 (FIG. 4). Accordingly, the insert 201 includes a spline cover 220 for each of the shell splines 136. Each spline cover 220 includes camming walls 242a and 242b that correspond to the cam surfaces 142a, 142b of the shell splines 136. The camming walls 242a and 242b extend from an inner surface of the body 210 to form an apex 244 that is aligned with the apex 144 of the respective shell spline 136. The spline covers 220 are configured to cap or cover shell splines 136 to protect the shell splines 136 from being damaged by the anvil splines 134. Additionally, the spline covers 220 may assist in guiding or clocking the anvil assembly 120 into alignment with the shell assembly 118. The camming walls 242a and 242b may extend below a bottom surface of the body 210. Alternatively, the camming walls 242a and 242b may have a bottom surface that is planar with a bottom surface of the body 210. The camming walls 242a and 242b may be defined a lower angle or taper than the shell splines 136.

The insert 201 maintains staple registration by allowing the anvil splines 134 of the anvil assembly 120 to engage the shell splines 136 of the shell assembly 118 during stapling. Specifically, the anvil splines 134 engage the spline covers 220 and then pass through the insert 201 to engage the anvil splines 134 such that the spline covers 220 may coarsely clock the anvil assembly 120 relative to the shell assembly 118 and the shell splines 136 may finely clock the anvil assembly 120 relative to the shell assembly 118.

By including the insert 201 to cover the cam surfaces 142a, 142b of the shell splines 136, the insert 201 may prevent shell damage and deformation during clamping. In addition, the insert 201 may allow for increased clamping forces when compared to a shell assembly 118 without the insert 201. Further, the insert 201 may eliminate the need to detect for spline crash as the insert 201 may clock the anvil assembly 120 relative to the shell assembly 118 without damage to the shell assembly 118 in an instance of spline crash. By eliminating the need to detect for spline crash, the insert 201 may allow for measurement of clamping force rather than to detect for spline crash such that failure of other parts of the shell assembly 118 and/or the anvil assembly 120 can be prevented. In addition, the strength of the anvil retainer 30 (FIG. 2) and/or the anvil shaft 124 can be increased to allow for greater clamping forces which may allow for thicker segments of tissue to be captured and/or stapled.

Figure 8:
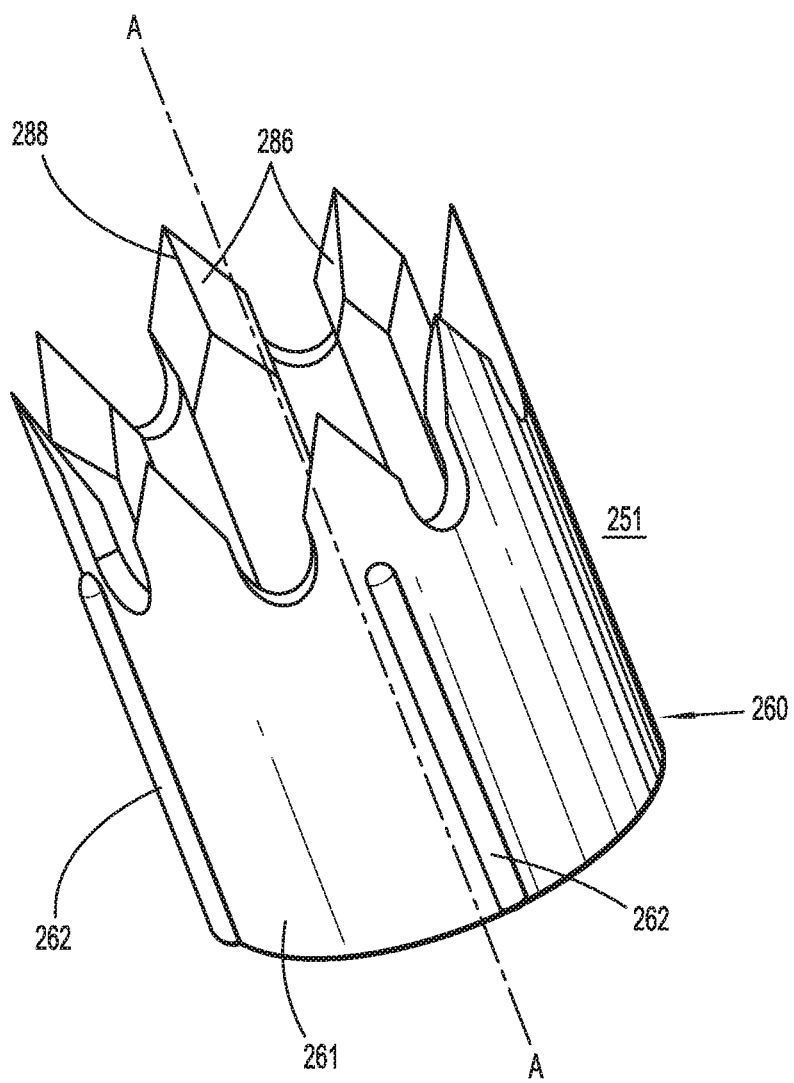
FIG. 8 is a perspective view of an exemplary embodiment of another insert for use with the shell assembly of the surgical stapling device of FIG. 1 and/or the shell assembly of the "Prior Art" surgical stapling device of FIG. 3.
Figure 9:
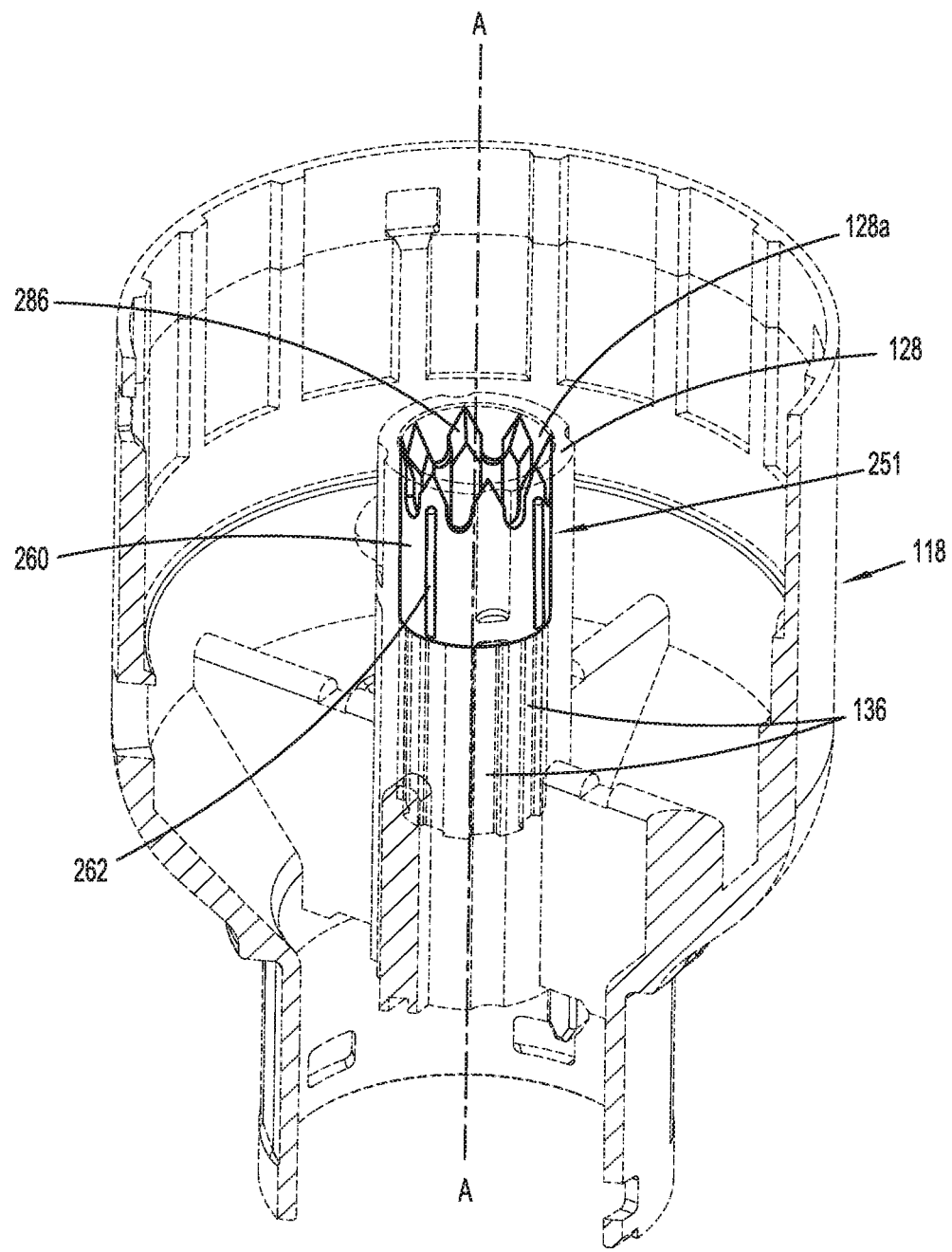
FIG. 9 is a perspective cutaway view of the shell assembly of the "Prior Art" surgical stapling device of FIG. 3 with the insert of FIG. 8 installed within the bore of the shell assembly.

Referring now to FIGS. 8 and 9, an insert 251 is provided in accordance with the present disclosure. The insert 251 is configured to be installed within the bore 128a of the shell assembly 118 to clock the anvil assembly 120 (FIG. 3) into alignment with the shell assembly 118. The insert 251 is formed of a metal, e.g., steel, and the shell splines 136 and the anvil splines 134 are generally formed of plastic. The insert 251 is configured to be installed or positioned within the bore 128a of the shell assembly 118 distal of the shell splines 136 to protect the shell splines 136 from damage as detailed below. In addition, the insert 251 is configured to retrofit existing shell assemblies 118 to enhance the clocking and/or to protect the shell splines 136 from damage. Specifically, the insert 251 is installed or positioned within the bore 128a of the shell assembly 118 before a surgical procedure. The insert 251 may be positioned by the manufacturer of the shell assembly 118 or may be positioned by a clinician before a surgical procedure.

The insert 251 has a body 260 in the form of a ring. The body 260 defines a longitudinal axis A-A and has an outer surface 261. The body 260 includes ribs 262 that protrude outward from the outer surface 261 and extend in a direction parallel to the longitudinal axis A-A. The height that the ribs 262 protrude from the outer surface 261 is less than or equal to a thickness of the body 260. For example, the height that the ribs 262 protrude from the outer surface 261 may be one-quarter, one-half, three-quarters, or equal to the thickness of the body 260.

The insert 251 also includes insert splines 286 extend radially inward from an inner surface of the body 260. The insert 251 may include an equal number of insert splines 286 to the number of shell splines 136 of the shell assembly 118 such that each of the insert splines 286 is configured to cover or protect each of the shell splines 136 as the anvil splines 134 (FIG. 3) are drawn through the bore 128a of the shell assembly 118 as described in greater detail below. In some embodiments, the insert 251 includes less insert splines 286 than the number of shell splines 136 of the shell assembly 118. The insert splines 286 may extend from a distal or leading end of the body 260. Specifically, the insert splines 288 may include a leading portion 288 that extends from the leading end of the body 260 such that the leading portion 288 of the insert splines 288 engage the anvil splines 134 before the shell splines 136 engage the anvil splines 134. The insert splines 286 may extend to a bottom or trailing end of the body 260 such that the anvil splines 134 (FIG. 3) may be simultaneously engaged with the insert splines 286 and the shell splines 136. In embodiments, the insert splines 286 also extend from the trailing end of the insert 251. Each of the insert splines 286 may have a width equal to a width of the shell splines 136 or alternatively, each of the insert splines 286 may have a width less than a width of the shell splines 136. The width of the shell splines being defined along the inner surface of the body 260 in a direction transverse to the longitudinal axis A-A.

With particular reference to FIG. 9, the insert 251 is installed into the bore 128a of the shell assembly 128 distal of the shell splines 136 such that the insert splines 286 are aligned with the shell splines 136. When the insert 251 is installed in the bore 128a, the longitudinal axis A-A of the insert 251 is coincident with the longitudinal axis A-A of the shell assembly 118. The ribs 262 of the insert 251 engage an inner surface of the inner housing portion 128 defining the bore 128a to prevent the insert 251 from rotating about the longitudinal axis A-A. In some embodiments, the inner housing portion 128 may define grooves in the inner surface of the inner housing portion 128 that receive the ribs 262 such that the insert splines 286 are aligned with the shell splines 136.

With additional reference back to FIG. 3, the insert 251 is installed within the bore 128a when the shell assembly 118 is coupled to the handle assembly 112. In some embodiments, the shell assembly 118 may be secured to the handle assembly 112 before the insert 251 is installed. When the insert 251 installed within the bore 128a and the shell assembly 118 secured to the handle assembly 112, the anvil retainer 130 is passed through the bore 128a of the shell assembly 118. With the anvil retainer 130 passed through the bore 128a, the anvil shaft 124 of the anvil assembly 120 is coupled to the anvil retainer 130. The anvil retainer 130 is then withdrawn through the shell assembly 118 to draw the anvil shaft 124 into the bore 128a. As the anvil shaft 124 is drawn in into the bore 128a, the anvil splines 134 engage the insert splines 286 to coarsely clock the anvil shaft 124, and thus the anvil assembly 120, relative to the shell assembly 118. As the anvil shaft 124 is drawn further through the bore 128a, the anvil splines 134 engage the shell splines 136 to finely clock the anvil shaft 124 relative to the shell assembly 118. The insert 251 maintains staple registration by allowing the anvil splines 134 of the anvil assembly 120 to engage the shell splines 136 of the shell assembly 118 during stapling.

By including the insert 251 to cover the shell splines 136, the insert 251 may prevent shell damage and deformation during clamping. In addition, the insert 251 may allow for increased clamping forces when compared to a shell assembly 118 without the insert 251. Further, the insert 251 may eliminate the need to detect for spline crash as the insert 251 may clock the anvil assembly 120 relative to the shell assembly 118 without damage to the shell assembly 118 in an instance of spline crash. By eliminating the need to detect for spline crash, the insert 251 may allow for measurement of clamping force rather than to detect for spline crash such that failure of other parts of the shell assembly 118 and/or the anvil assembly 120 can be prevented. In addition, the strength of the anvil retainer 30 (FIG. 2) and/or the anvil shaft 124 can be increased to allow for greater clamping forces which may allow for thicker segments of tissue to be captured and/or stapled.

Figure 10:
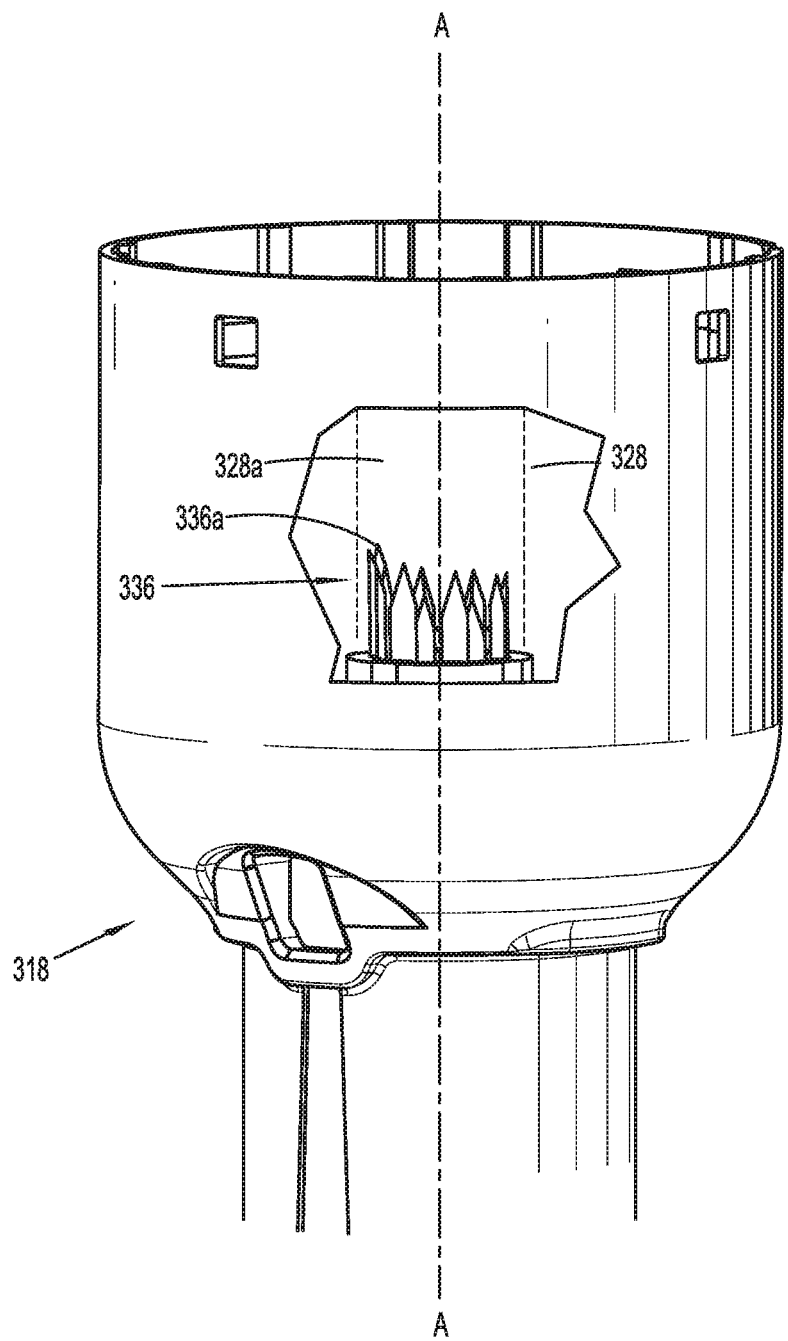
FIG. 10 is a side cutaway view of the shell assembly of the prior art surgical stapling device of FIG. 3 with the insert of FIG. 8 installed within the bore of the shell assembly.
Figure 11:
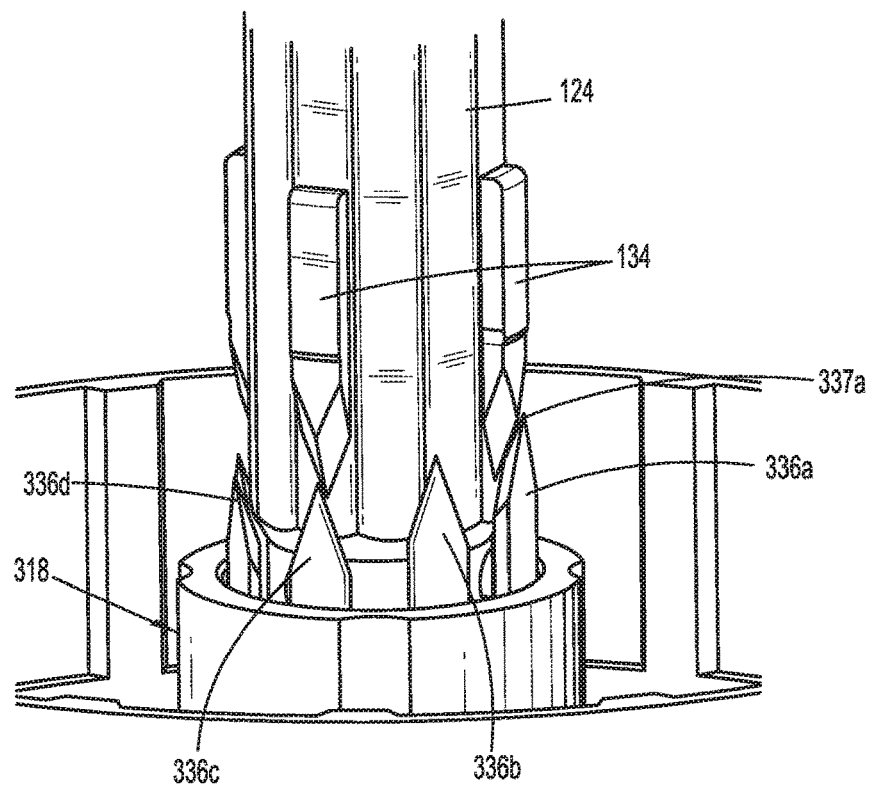
FIG. 11 is an enlarge view of the an anvil shaft of the anvil assembly of FIG. 3 being drawn through the insert of FIG. 8.
Figure 12:
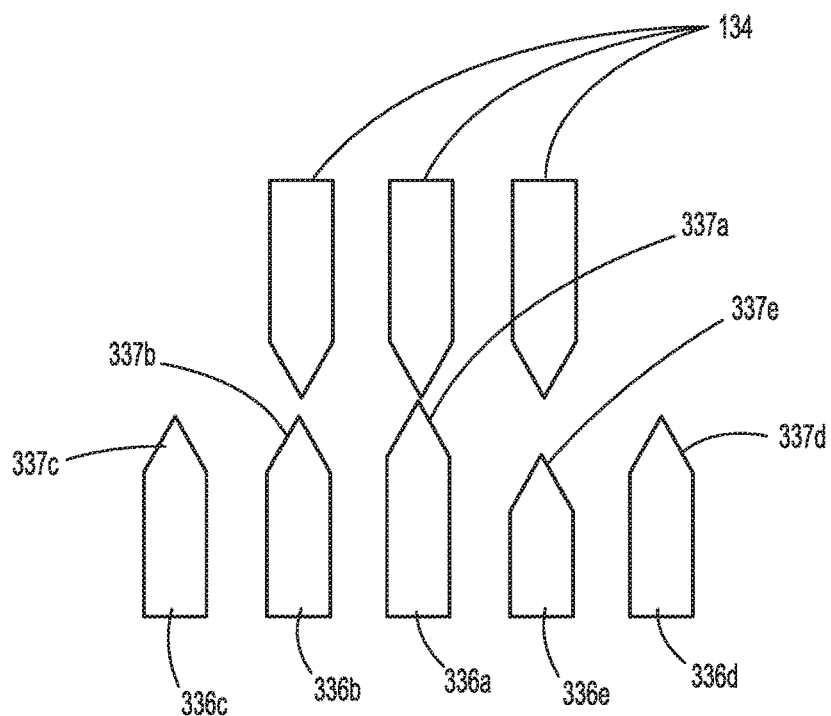
FIG. 12 is a schematic view of an insert spline configuration of the insert of FIG. 8.

With reference to FIGS. 10-12, a shell assembly 318 is provided in accordance with the present disclosure. The shell assembly 318 is similar to the shell assembly 18 detailed above, as such for reasons of brevity only the differences will be detailed herein.

The shell assembly 318 includes an inner housing portion 328 defining a longitudinal axis A-A. The inner housing portion 328 has an inner wall that defines a bore 328a about the longitudinal axis A-A. The bore 328a extends entirely through the shell assembly 318. The shell assembly 318 includes shell splines 336 that are positioned on the inner wall and extend into the bore 328a.

The shell splines 336 include a lead spline 336a having a height greater than each of the other splines 336, e.g., splines 336b-336e. Specifically, a leading end 337a of the lead spline 336a is positioned distal of a leading end 337b-337e of the other splines 336b-336e along the longitudinal axis A-A. The height of the shell splines 336 being defined in a direction along the longitudinal axis A-A. The height of each of the other splines 336b-336e may also vary with respect to one another or the height of each of the other splines 336b-336e may be equal to one another.

With particular reference to FIG. 12, by having a lead spline 336a with a height greater than the other splines 336b-e, the anvil splines 134 of the anvil shaft 124 (FIG. 3) engage the leading end 337a of the lead spline 336a before engaging the other splines 336b-336e such that the anvil shaft 124 is clocked relative to the shell assembly 318 to prevent anvil splines 134 from straddling the splines 336. In addition, by varying the heights of the splines 336, another spline 336b-336e may act as a lead spline when the anvil shaft 124 is oriented with the shell 318 such that none of the anvil splines 134 engage the lead spline 336a.

By varying the heights of the splines 336a-336e, spline crash due to straddling may be eliminated. In addition, varying the heights of the splines 336a-336e may prevent the anvil shaft 124 from jamming within the shell assembly 318. Further, varying the heights of the splines 336a-336e may reduce clamping forces required to clamp tissue when compared to the shell assembly 118. Particulates within the shell assembly 318 may also be reduced as a result of eliminating straddling, preventing jamming, and reducing clamping forces.

Figure 13:
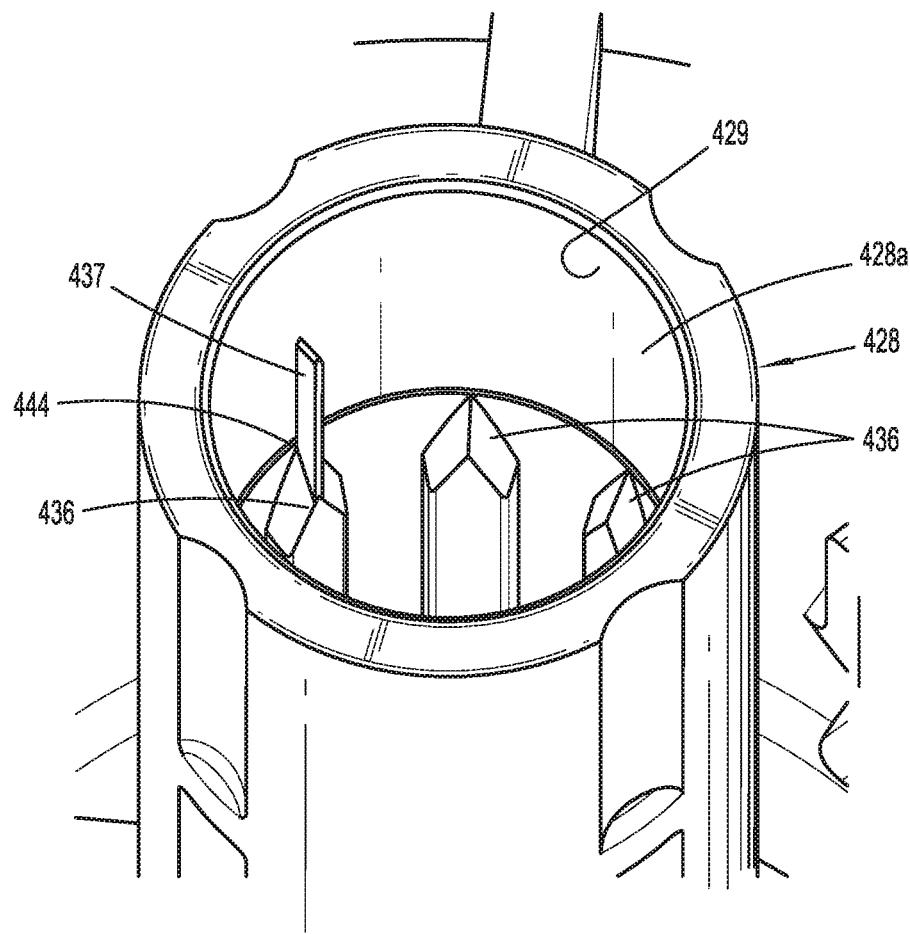
FIG. 13 is an enlarged perspective view of an exemplary embodiment of a shell spline configuration of another shell assembly provided in accordance with the present disclosure having a flexible tine.
Figure 14:
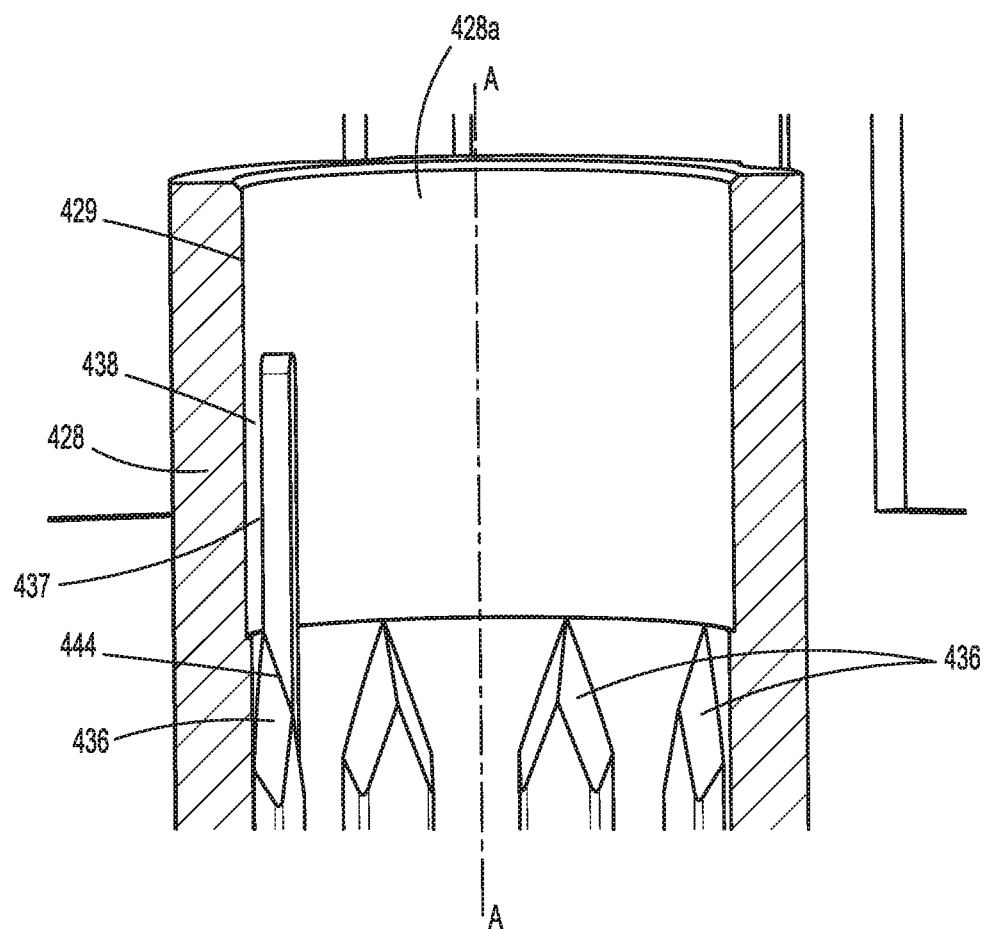
FIG. 14 is a side, cutaway view of the shell assembly of FIG. 13.
Figure 15:
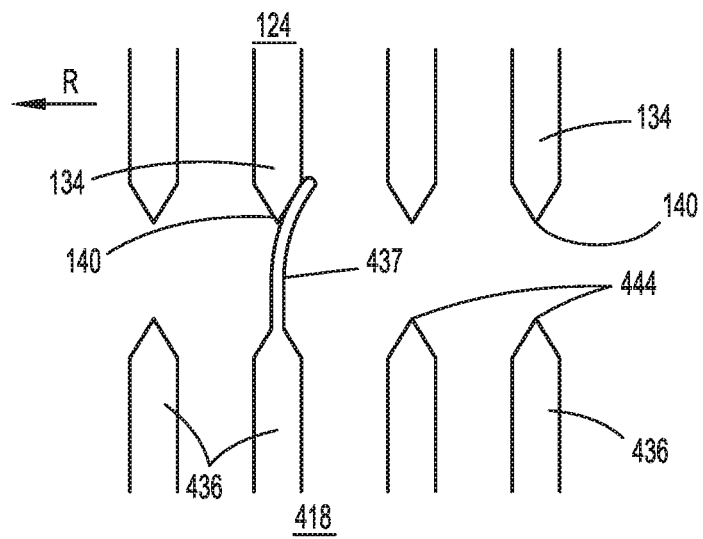
FIG. 15 is a schematic view of the shell spline configuration of the insert of FIG. 13.

Referring now to FIGS. 13-15, a shell assembly 418 is provided in accordance with the present disclosure. The shell assembly 418 is similar to the shell assembly 18 detailed above, as such for reasons of brevity only the differences will be detailed herein.

The shell assembly 418 includes an inner housing portion 428 defining a longitudinal axis A-A. The inner housing portion 428 includes an inner wall 429 that defines a bore 428a about the longitudinal axis A-A. The bore 428a extends entirely through the shell assembly 418. The shell assembly 418 includes shell splines 436 positioned on the inner wall 429 and that extend into the bore 428a.

One of the shell splines 436 includes a flexible tine 437 extending distally in a direction parallel to the longitudinal axis A-A. The flexible tine 437 extends from an apex 444 of the respective shell spline 436. With particular reference to FIG. 14, the flexible tine 437 is secured to the apex 444 and is spaced apart from the inner wall 429 to define a gap 438 therebetween such that the flexible tine 437 is not directly attached to the inner wall 429.

As shown, the flexible tine 437 has a negligible width; however, the flexible tine 437 may have a width up to about one half the width of the respective shell spline 436. In such embodiments, the flexible tine 437 may have a wedge tip having an apex to engage the anvil splines 134 of the anvil shaft 124.

With specific reference to FIG. 15, the flexible tine 437 is configured to engage one of the anvil splines 134 as the anvil shaft 124 is drawn through the bore 428a and to clock the anvil shaft 124 relative to the shell assembly 418 in the direction indicated by arrow "R". The flexible tine 437 is configured to coarsely clock the anvil shaft 124 such that each of the apexes 140 of the anvil splines 134 are offset to the same side of a respective apex 444 of the shell splines 436. By offsetting each of the apexes 140 of the anvil splines 134, straddling of the shell splines 436 with the anvil splines 134 can be eliminated. Once the flexible tine 437 coarsely clocks the anvil shaft 124 to offset the apexes 140 of the anvil splines 134 from the apexes 444 of the shell splines 436, additional movement of the anvil shaft 124 into the shell assembly 418 causes the anvil splines 134 to engage the shell splines 436 to finely clock the anvil shaft 124 with the shell assembly 436.

As shown in FIG. 15, the flexible tine 437 is configured to deflect in a direction transverse to the longitudinal axis A-A as the flexible tine 437 is engaged by one of the anvil splines 134. By deflecting in response to being engaged by one of the anvil splines 134, the flexible tine 437 may be prevented from damaging the anvil splines 134. The distal or leading end of the flexible tine 437 may be blunt to prevent the flexible tine 437 from damaging the anvil splines 134.

Referring now to FIG. 16, a shell assembly 518 is provided in accordance with the present disclosure. The shell assembly 518 is similar to the shell assembly 18 detailed above, as such for reasons of brevity only the differences will be detailed herein.

The shell assembly 518 includes an inner housing portion 528 defining a longitudinal axis A-A. The inner housing portion 528 defines a bore 528a about the longitudinal axis A-A that extends entirely through the shell assembly 518. The shell assembly 518 includes shell splines 536 that are positioned on an inner wall defining the bore 528a and that extend into the bore 528a. Each of the shell splines 536 defines a spline axis S-S that passes through an apex 544 of the shell spline 536 and is parallel to the longitudinal axis A-A.

One or more of the shell splines 536 includes a tine 537 that extends distally from an apex 544 of the spline 536 along the spline axis S-S. The tine 537 includes a leading portion 538 which has a leading tip 539 offset from the spline axis S-S such that a biased leading edge of the leading portion 538 is configured to rotate or deflect another spline, e.g., anvil spline 134 (FIG. 3) from crashing with the apex 544 of the spline 536.

The leading tip 539 of one tine 537 may be longitudinally offset from the leading tip 539 of another one of the tines 537 such that the leading tip 539 of one tine 537 is engaged before the leading tip 539 of the other tines 537. The tines 537 may be secured to the inner wall that defines the bore 528a.

With reference to FIGS. 17A and 17B, the anvil shaft 124 is drawn into the bore 528a of the shell assembly 518 with the apex 140 of the anvil spline 134 offset from the spline axis S-S. As the anvil shaft 134 is drawn into the bore 528a, the anvil spline 134 engages the leading tip 539 of the tine 537. The engagement of the anvil spline 134 with the tine 537 clocks the anvil shaft 124 relative to the shell assembly 518 in the direction indicated by arrow "A" when the apex 140 of the anvil spline 134 is offset to the spline axis S-S beyond the leading tip 539 of the tine 537. Specifically, when the anvil spline 134 engages the tine 537, the tine 537 coarsely clocks the anvil shaft 124 with respect to the shell assembly 518 in a direction indicated by arrow "A". When the anvil shaft 124 is drawn further through the bore 528a the anvil spline 134 engages the shell spline 536 to finely clock the anvil shaft 124 relative to the shell assembly 518.

Referring now to FIGS. 18A and 18B, the anvil shaft 124 is drawn into the bore 528a of the shell assembly 518 with the apex 140 of the anvil spline 134 aligned with the spline axis S-S. As the anvil shaft 134 is drawn into the bore 528a, the anvil spline 134 engages the leading edge of the leading portion 538 of the tine 537. The engagement of the anvil spline 134 with the leading edge of the tine 537 clocks the anvil shaft 124 relative to the shell assembly 518 in the direction indicated by arrow "B". Specifically, when the anvil spline 134 engages the tine 537, the tine 537 coarsely clocks the anvil shaft 124 with respect to the shell assembly 518 in a direction indicated by arrow "B". When the anvil shaft 124 is drawn further through the bore 528a the anvil spline 134 engages the shell spline 536 to finely clock the anvil shaft 124 relative to the shell assembly 518.

Figure 19:
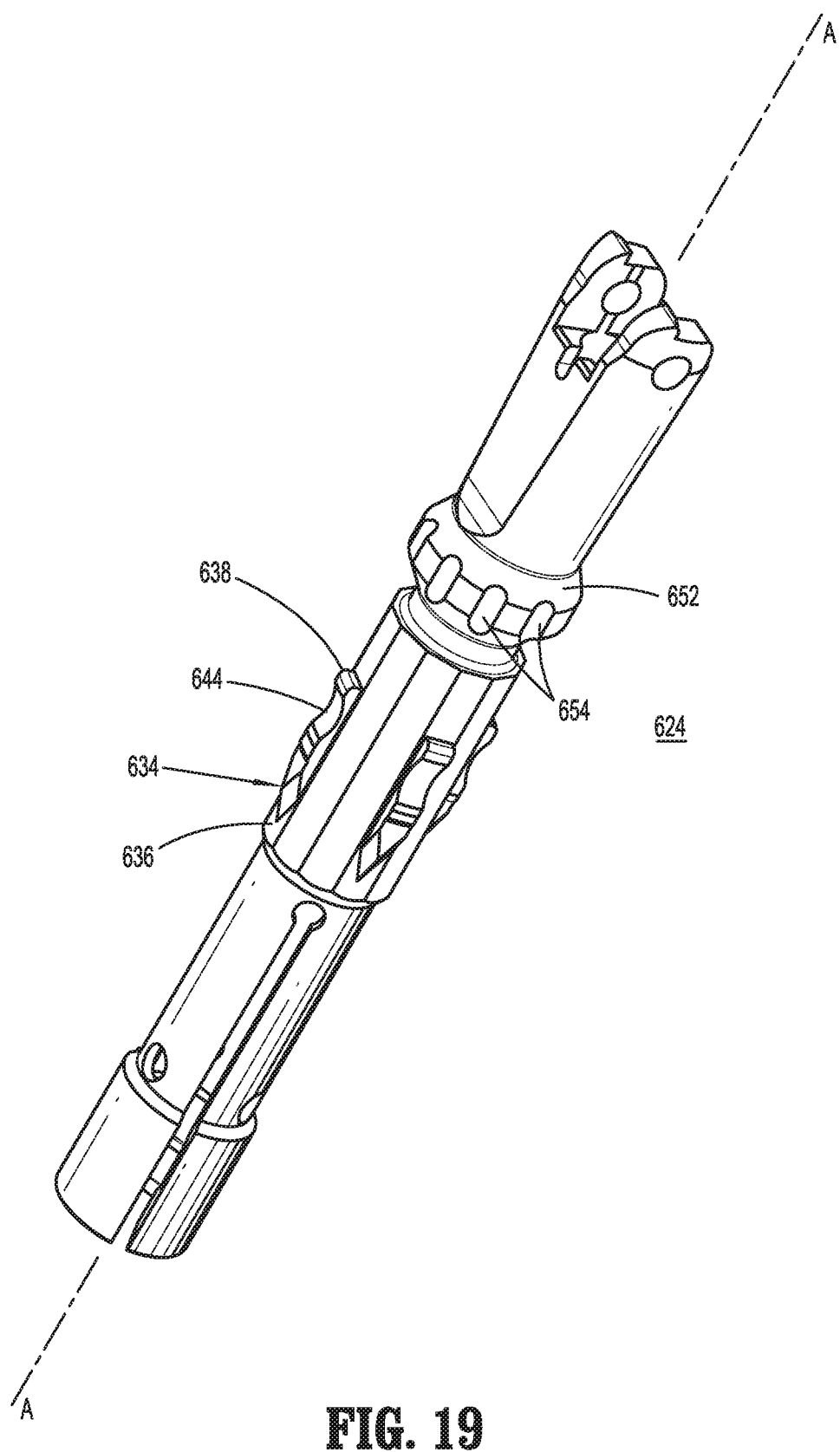
FIG. 19 is a perspective view of an exemplary embodiment of an anvil shaft provided in accordance with the present disclosure.
Figure 20:
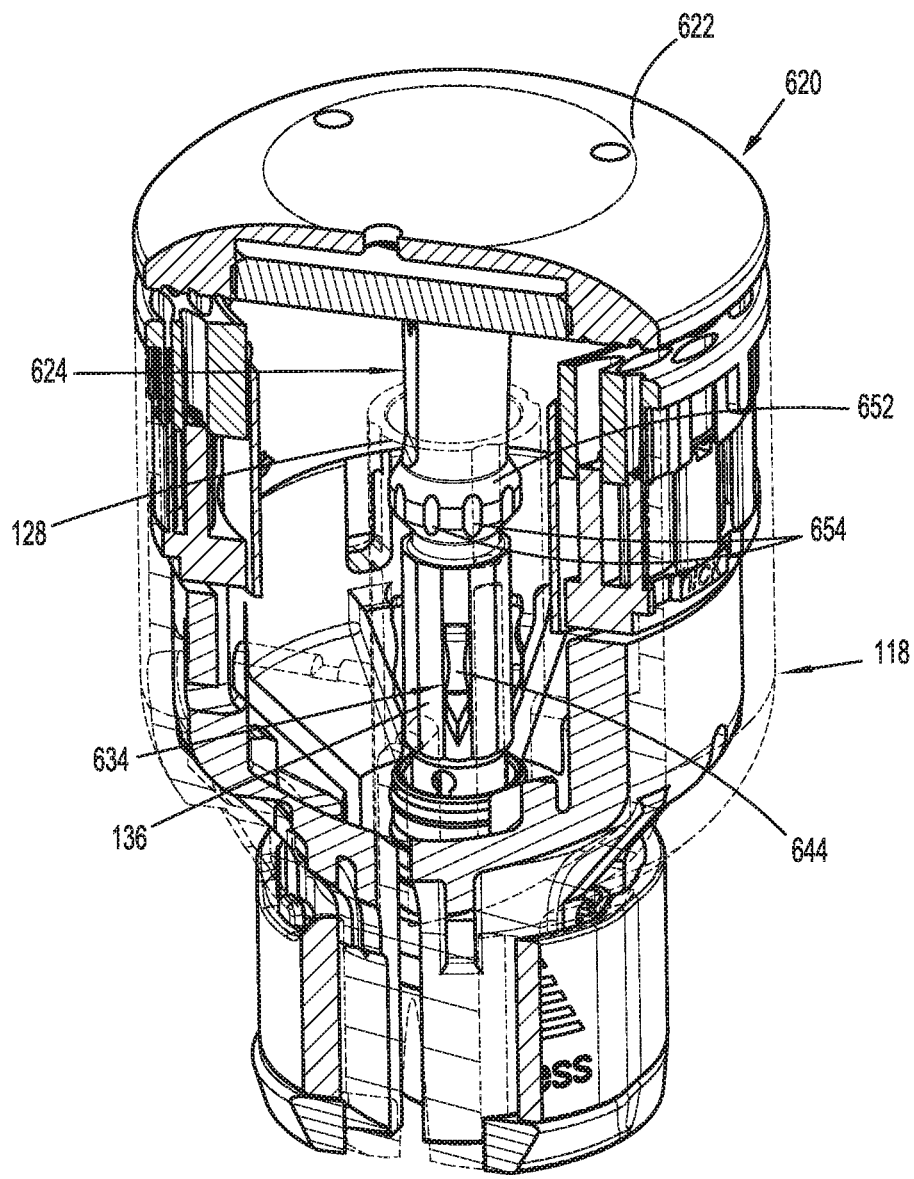
FIG. 20 is a perspective cutaway view of an anvil assembly including the anvil shaft of FIG. 19 approximated with the "Prior Art" shell assembly of FIG. 3.

Referring now to FIGS. 19 and 20, an anvil shaft 624 is provided in accordance with the present disclosure. The anvil shaft 624 may be part of an anvil assembly 620 that also includes an anvil head 622. The anvil assembly 620 is similar to the anvil assembly 20 (FIG. 1) detailed above, as such only the differences will be detailed for reasons of brevity.

The anvil shaft 624 defines a longitudinal axis A-A and includes a plurality anvil splines 634 disposed about an outer surface of the anvil shaft 624. Each of the anvil splines 634 extend along the outer surface of the anvil shaft 624 in a direction parallel with the longitudinal axis A-A. Each of the anvil splines 634 has a leading portion 636, a trailing portion 638, and a relief cutout 644 between the leading and trailing portions 636, 638. Specifically, the relief cutout 644 reduces an overall contact surface area of an outer surface and/or side surfaces of the anvil spline 634 with the shell assembly, e.g., shell assembly 118, while maintaining the engagement between the anvil splines 634 and the shell splines 136 to maintain staple registration. The relief cutout 644 may reduce an extent that the anvil spline 634 extends from the outer surface of the anvil shaft 624 and/or may reduce a width of the anvil spline 634.

The anvil shaft 624 also includes a boss 652 positioned in a distal portion of the anvil shaft 624. The boss 652 is similar to a boss 152 (FIG. 3) of the anvil shaft 124. The boss 652 is substantially donut or toroid in shape with an outer surface that defines a plurality of relief pockets 654. The plurality of relief pockets reduces a surface area of the outer surface of the boss 652 when compared to an outer surface of the boss 152.

The boss 652 is configured to be received in the inner housing portion 128 of the shell assembly 118 when the anvil assembly 620 is approximated with the shell assembly 118 to coaxially align the anvil shaft 624 with the inner housing portion 128 of the shell assembly 118. Specifically, the boss 652 is received within the inner housing portion 128 when tissue is clamped between the anvil head 622 and the shell assembly 118 and before staples are fired through tissue from the shell assembly 118.

With particular reference to FIG. 20, the relief cutouts 644 and/or relief pockets 654 of the anvil shaft 624 reduce a surface area of the anvil shaft 624 which engages features of the shell assembly 118 to reduce friction or drag between the anvil shaft 624 and the shell assembly 118. Specifically, the relief cutouts 644 reduce the surface area of the anvil splines 634 that engage the inner housing portion 128 and the shell splines 136 of the shell assembly 118. When boss 652 is received in a distal portion of the inner housing portion 128 of the shell assembly 118 to coaxially align the anvil shaft 624 with the shell assembly 118, the relief pockets 654 reduce a surface area of the boss 652 that engages the inner housing portion 128 such that friction or drag between the anvil shaft 624 and the shell assembly 118 is reduced when compared to the boss 152 (FIG. 3).

By reducing the friction or drag between the anvil shaft 624 and the shell assembly 118, a clamping force required to be exerted on the anvil shaft 624 by the anvil retainer 130 (FIG. 3) to approximate the anvil assembly 620 relative to the shell assembly 118 can be reduced compared to a clamping force required to approximate the anvil assembly 120 relative to the shell assembly 118. Reducing the required clamping force may reduce wear on an adapter and/or a handle assembly, e.g., handle assembly 12 (FIG. 1). Reducing the required clamping force may also improve spline crash detection by reducing noise in strain gauges resulting from the clamping forces. Reducing the required clamping force may also increase confidence of a clinician in spline crash detection by reducing false spline crash detections.

As shown, the anvil shaft 624 includes anvil splines 634 that define relief cutouts 644 and a boss 652 that defines relief pockets 654. In embodiments, the anvil shaft 624 includes a boss 652 that defines relief pockets 654 without having anvil splines 634 that define relief cutouts 644. It will be appreciated that the boss 652 may be used with any suitable anvil shaft, e.g., anvil shaft 124, to reduce the frictional engagement of the anvil shaft with the shell assembly. In some embodiments, the anvil shaft includes anvil splines 634 that define relief cutouts 644 without having a boss 652 that defines relief pockets 654. It will be appreciated that any suitable anvil spline, e.g., anvil spline 134, may be modified to include a relief cutout 644 to reduce the frictional engagement of the anvil spline with shell splines, e.g., shell splines 136.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. An insert for a surgical stapler, the insert comprising:
   a body configured to fit within a bore of a shell assembly; and
   spline covers extending inward from the body, each spline cover sized and dimensioned to cap a distal portion of splines of the shell assembly.

2. The insert according to claim 1, wherein the body has a ring shape.

3. The insert according to claim 1, wherein the spline covers are made of metal.

4. The insert according to claim 1, wherein the insert is monolithically formed.

5. The insert according to claim 1, wherein each of the spline covers includes a first camming wall and a second camming wall that form an apex at an intersection of the first and second camming walls.

6. The insert according to claim 1, wherein the body includes a top surface and a bottom surface, at least one of the spline covers extending below the bottom surface.

7. A surgical stapler comprising:
   an anvil assembly including an anvil shaft having a plurality of anvil splines radially disposed about the anvil shaft;
   a shell assembly defining a bore about a central longitudinal axis thereof and including a plurality of shell splines radially disposed on a wall defining the bore such that the plurality of shell splines extend into the bore; and
   an insert disposed within the bore and having a body and spline covers extending inward from the body, each spline cover sized and dimensioned to cap a distal portion of a respective shell spline of the plurality of shell splines such that each of the plurality of shell splines is capped by a respective spline cover.

8. The surgical stapler according to claim 7, wherein the plurality of shell splines are made of plastic and each of the spline covers is made of metal.

9. The surgical stapler according to claim 7, further comprising a handle assembly including an anvil retainer, the shell assembly supported on a distal portion of the handle assembly, the anvil retainer configured to pass through the bore of the shell assembly to engage and draw the anvil shaft through the bore of the shell assembly.

10. The surgical stapler according to claim 7, wherein the plurality of anvil splines are configured to engage the spline covers to clock the anvil assembly relative to the shell assembly such that each anvil spline of the plurality of anvil splines is disposed between adjacent shell splines of the plurality of shell splines.

11. The surgical stapler according to claim 7, wherein each shell spline of the plurality of shell splines includes a first cam surface and a second cam surface, each spline cover including a first camming wall and a second camming wall configured to cover the first cam surface and the second cam surface, respectively.

12. The surgical stapler according to claim 7, wherein the first and second cam surfaces are tapered at a first angle and the first and second camming walls are tapered at a second angle which is less than the first angle.

13. The surgical stapler according to claim 7, wherein the shell assembly includes a staple cartridge having a plurality of staples, the plurality of anvil splines engaged with the plurality of shell splines to radially align the anvil assembly with the shell assembly during firing of the plurality of staples.

14. A method of stapling tissue, the method comprising:
positioning an insert within a bore of a shell assembly of a surgical stapler, the insert including spline covers and the shell assembly including shell splines that extend into the bore, positioning the insert within the bore including each spline cover capping a respective one of the shell splines; and drawing an anvil shaft of an anvil assembly into the bore of the shell assembly such that an anvil spline disposed on an outer surface of the anvil shaft engages one of the spline covers to clock the anvil assembly relative to the shell assembly.

15. The method according to claim 14, further comprising further drawing the anvil shaft into the bore of the shell assembly such that the anvil spline engages the shell splines to radially align the anvil assembly with the shell assembly.

16. The method according to claim 14, wherein the anvil spline engaging one of the spline covers coarsely clocks the anvil assembly relative to the shell assembly and the anvil spline engaging the shell spline finely clocks the anvil assembly relative to the shell assembly.

17. The method according to claim 14, further comprising securing the shell assembly to a distal portion of a handle assembly of a surgical stapler.

18. The method according to claim 14, further comprising extending an anvil retainer of the handle assembly distally through the bore of the shell assembly and coupling the anvil shaft to the anvil retainer.

19. The method according to claim 14, wherein drawing the anvil shaft into the bore includes actuating a knob of the handle assembly to draw the anvil shaft into the bore.

* * * * *